United States Patent
De Souza Rodrigues et al.

(10) Patent No.: US 11,793,836 B2
(45) Date of Patent: Oct. 24, 2023

(54) METHOD FOR TREATING COMPLICATIONS RELATED TO ACUTE OR CHRONIC HYPERGLYCEMIA

(71) Applicants: INMUNE BIO INC., La Jolla, CA (US); EMORY UNIVERSITY, Atlanta, GA (US)

(72) Inventors: Maria Elizabeth De Souza Rodrigues, Atlanta, GA (US); Maria de Lourdes Gamez Tansey, Atlanta, GA (US); Christopher J. Barnum, Detroit, MI (US); Raymond J. Tesi, Martha's Vineyard, MA (US); Dean P. Jones, Atlanta, GA (US); Douglas I. Walker, Atlanta, GA (US)

(73) Assignees: INmune Bio Inc, Boca Raton, FL (US); EMORY UNIVERSITY, Atlanta, GA (US)

( * ) Notice: Subject to any disclaimer, the term of this patent is extended or adjusted under 35 U.S.C. 154(b) by 0 days.

(21) Appl. No.: 16/652,407

(22) PCT Filed: Sep. 27, 2018

(86) PCT No.: PCT/US2018/053227
§ 371 (c)(1),
(2) Date: Mar. 30, 2020

(87) PCT Pub. No.: WO2019/067789
PCT Pub. Date: Apr. 4, 2019

(65) Prior Publication Data
US 2020/0289576 A1    Sep. 17, 2020

Related U.S. Application Data

(60) Provisional application No. 62/735,774, filed on Sep. 24, 2018, provisional application No. 62/564,232, filed on Sep. 27, 2017.

(51) Int. Cl.
| | |
|---|---|
| *A61P 3/10* | (2006.01) |
| *A61K 35/28* | (2015.01) |
| *A61K 48/00* | (2006.01) |
| *C07K 14/525* | (2006.01) |
| *G01N 33/68* | (2006.01) |
| *A61K 38/00* | (2006.01) |

(52) U.S. Cl.
CPC ............ *A61K 35/28* (2013.01); *A61K 48/005* (2013.01); *A61P 3/10* (2018.01); *C07K 14/525* (2013.01); *G01N 33/68* (2013.01); *A61K 38/00* (2013.01); *G01N 2333/82* (2013.01)

(58) Field of Classification Search
CPC .......... C07K 14/525; A61K 35/28; A61P 3/10
See application file for complete search history.

(56) References Cited

PUBLICATIONS

MacPherson et al., Neurobiol. 102:81-95, (2017).*
Martinez et al., Neural Regen. Research 14: 1158-1176, (2019).*

* cited by examiner

*Primary Examiner* — Gyan Chandra
(74) *Attorney, Agent, or Firm* — Joshua S. Schoonover

(57) ABSTRACT

The disclosure concerns a method of treating complications of acute or chronic hyperglycemia and/or diet-induced obesity comprising: (i) determining whether a patient suffers from complications related to acute or chronic hyperglycemia and/or diet induced obesity, and if so, (ii) administering to the patient in need thereof a selective inhibitor of soluble TNF-α but not transmembrane TNF-α. For purposes herein, complications of acute or chronic hyperglycemia and/or diet-induced obesity include: diabetes mellitus, insulin resistance, hepatic steatosis, non-alcoholic hepatic steatosis, fibrotic liver disease, vascular disease, and chronic intestinal inflammation.

17 Claims, 14 Drawing Sheets
Specification includes a Sequence Listing.

| 1   | atgcaccacc | accaccacca | cgtacgctcc | tcctcccgca | ctccgtccga | caaaccggta |
|-----|------------|------------|------------|------------|------------|------------|
| 61  | gctcacgtag | tagctaaccc | gcaggctgaa | ggtcagctgc | agtggctgaa | ccgccgcgct |
| 121 | aacgctctgc | tggctaacgg | tgtagaactg | cgcgacaacc | agctggtagt | accgtccgaa |
| 181 | ggtctgtacc | tgatctactc | ccaggtactg | ttcaaaggtc | agggttgtcc | gtccactcac |
| 241 | gtactgctga | ctcacactat | ctcccgcatc | gctgtatcct | accagactaa | agtaaacctg |
| 301 | ctgtccgcta | tcaaatcccc | gtgtcagcgc | gaaactccgg | aaggtgctga | agctaaaccg |
| 361 | tggtacgaac | cgatctacct | gggtggtgta | ttccagctgg | aaaaaggtga | ccgcctgtcc |
| 421 | gctgaaatca | accgcccgga | ctacctggac | ttcgctgaat | ccggtcaggt | atacttcggt |
| 481 | atcatcgctc | tgtga      |            |            |            |            |

(SEQ ID NO:1)

FIG.1A

| 1   | MHHHHHHVRS | SSRTPSDKPV | AHVVANPQAE | GQLQWLNRRA | NALLANGVEL | RDNQLVVPSE |
|-----|------------|------------|------------|------------|------------|------------|
| 61  | GLYLIYSQVL | FKGQGCPSTH | VLLTHTISRI | AVSYQTKVNL | LSAIKSPCQR | ETPEGAEAKP |
| 121 | WYEPIYLGGV | FQLEKGDRLS | AEINRPDYLD | FAESGQVYFG | IIAL       |            |

(SEQ ID NO:2)

FIG.1B

Val Arg Ser Ser Ser Arg Thr Pro Ser Asp Lys Pro Val Ala His Val Val Ala Asn Pro Gln Ala Glu
Gly Gln Leu Gln Trp Leu Asn Arg Arg Ala Asn Ala Leu Leu Ala Asn Gly Val Glu Leu Arg Asp
Asn Gln Leu Val Val Pro Ser Glu Gly Leu Tyr Leu Ile Tyr Ser Gln Val Leu Phe Lys Gly Gln
Gly Cys Pro Ser Thr His Val Leu Leu Thr His Thr Ile Ser Arg Ile Ala Val Ser Tyr Gln Thr Lys
Val Asn Leu Leu Ser Ala Ile Lys Ser Pro Cys Gln Arg Glu Thr Pro Glu Gly Ala Glu Ala Lys Pro
Trp Tyr Glu Pro Ile Thr Leu Gly Gly Val Phe Gln Leu Glu Lys Gly Asp Arg Leu Ser Ala Glu Ile
Asn Arg Pro Asp Tyr Leu Asp Phe Ala Glu Ser Gly Gln Val Tyr Phe Gly Ile Ile Ala Leu (SEQ ID NO:3)

FIG.1C

| Wild-type TNF amino acid | Wild-type TNF amino acid number | Mutants |
|---|---|---|
| Q | 21 | R |
| N | 30 | D |
| R | 31 | I, D, E |
| R | 32 | D, E, S |
| A | 33 | E |
| A | 35 | S |
| K | 65 | D, T, M, W, I, Q, S, N, V, E |
| G | 66 | Q, K |
| Q | 67 | D, W, Y, R, K, S |
| A | 111 | R, E |
| K | 112 | D, E |
| Y | 115 | Q, K, E, N, R, F, H, M, L, I, W, D, T, S |
| D | 140 | R, K |
| D | 143 | E, N, Q, S, R, K |
| F | 144 | N |
| A | 145 | R, D, K, N, H, T, Q, E, Y, M, S, F |
| E | 146 | N, K, R, S |
| S | 147 | R |

SEQUENCE LISTING

<160> NUMBER OF SEQ ID NOS: 3

<210> SEQ ID NO 1
<211> LENGTH: 495
<212> TYPE: DNA
<213> ORGANISM: Homo sapiens

<400> SEQUENCE: 1

```
atgcaccacc accaccaca cgtacgctcc tcctcccgca ctccgtccga caaaccggta      60
gctcacgtag tagctaaccc gcaggctgaa ggtcagctgc agtggctgaa ccgccgcgct     120
aacgctctgc tggctaacgg tgtagaactg cgcgacaacc agctggtagt accgtccgaa     180
```

-continued

```
ggtctgtacc tgatctactc ccaggtactg ttcaaaggtc agggttgtcc gtccactcac    240
gtactgctga ctcacactat ctcccgcatc gctgtatcct accagactaa agtaaacctg    300
ctgtccgcta tcaaatcccc gtgtcagcgc gaaactccgg aaggtgctga agctaaaccg    360
tggtacgaac cgatctacct gggtggtgta ttccagctgg aaaaaggtga ccgcctgtcc    420
gctgaaatca accgcccgga ctacctggac ttcgctgaat ccggtcaggt atacttcggt    480
atcatcgctc tgtga                                                    495
```

<210> SEQ ID NO 2
<211> LENGTH: 164
<212> TYPE: PRT
<213> ORGANISM: Homo sapiens

<400> SEQUENCE: 2

Met His His His His His Val Arg Ser Ser Arg Thr Pro Ser
1               5                   10                  15

Asp Lys Pro Val Ala His Val Val Ala Asn Pro Gln Ala Glu Gly Gln
            20                  25                  30

Leu Gln Trp Leu Asn Arg Arg Ala Asn Ala Leu Leu Ala Asn Gly Val
        35                  40                  45

Glu Leu Arg Asp Asn Gln Leu Val Val Pro Ser Glu Gly Leu Tyr Leu
    50                  55                  60

Ile Tyr Ser Gln Val Leu Phe Lys Gly Gln Gly Cys Pro Ser Thr His
65                  70                  75                  80

Val Leu Leu Thr His Thr Ile Ser Arg Ile Ala Val Ser Tyr Gln Thr
                85                  90                  95

Lys Val Asn Leu Leu Ser Ala Ile Lys Ser Pro Cys Gln Arg Glu Thr
            100                 105                 110

Pro Glu Gly Ala Glu Ala Lys Pro Trp Tyr Glu Pro Ile Tyr Leu Gly
        115                 120                 125

Gly Val Phe Gln Leu Glu Lys Gly Asp Arg Leu Ser Ala Glu Ile Asn
    130                 135                 140

Arg Pro Asp Tyr Leu Asp Phe Ala Glu Ser Gly Gln Val Tyr Phe Gly
145                 150                 155                 160

Ile Ile Ala Leu

<210> SEQ ID NO 3
<211> LENGTH: 157
<212> TYPE: PRT
<213> ORGANISM: Homo sapiens

<400> SEQUENCE: 3

Val Arg Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Cys Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

```
Ile Lys Ser Pro Cys Gln Arg Glu Thr Pro Glu Gly Ala Glu Ala Lys
            100                 105                 110

Pro Trp Tyr Glu Pro Ile Thr Leu Gly Gly Val Phe Gln Leu Glu Lys
        115                 120                 125

Gly Asp Arg Leu Ser Ala Glu Ile Asn Arg Pro Asp Tyr Leu Asp Phe
        130                 135                 140

Ala Glu Ser Gly Gln Val Tyr Phe Gly Ile Ile Ala Leu
145                 150                 155
```

METHOD FOR TREATING COMPLICATIONS RELATED TO ACUTE OR CHRONIC HYPERGLYCEMIA

CROSS-REFERENCE TO RELATED APPLICATIONS

This application is a § 371 U.S. national phase entry of PCT/US2018/053227, filed Sep. 27, 2018;

which claims benefit of priority with U.S. Provisional Application Ser. No. 62/735,774, filed Sep. 24, 2018; and further claims benefit of priority with U.S. Provisional Application Ser. No. 62/564,232, filed Sep. 27, 2017;

the entire contents of each of which are hereby incorporated by reference.

TECHNICAL FIELD

The invention relates generally to the peripheral administration of a selective inhibitor of soluble TNF-α, preferably a dominant negative TNF-α protein, for the treatment of complications related to acute or chronic hyperglycemia, including insulin resistance.

BACKGROUND ART

High-fat high-carbohydrate diet and psychological stress are risk factors for insulin resistance in the brain and periphery. Diet and stress are important environmental factors that impact energetic balance. Overlapping mechanisms present in obesity can impair insulin functions and promote neurodegenerative mechanisms.

In addition to insulin resistance, a high-fat high-carbohydrate diet and psychological stress also tend to cause other complications related to acute or chronic hyperglycemia, for example hypercholesterolemia among other complications known to one having skill in the art.

A high-fat high-carbohydrate diet promotes changes in intestine tight junction proteins in association with colonic inflammation. For instance, increased intestinal leakiness associated with tight junction proteins alterations allows for products of the intestinal tract produced by the microbiome to promote systemic effects including systemic inflammation.

The high-fat high-carbohydrate diet promotes metabolic changes in the liver, which can result in hepatic dysfunction and can cause fat deposition also known as steatosis. For example, it is known that a high-fat high-carbohydrate diet can cause hepatic steatosis, non-alcoholic fatty liver disease (NAFLD), non-alcoholic steatohepatitis (NASH), cirrhosis and liver failure.

Stress can elicit changes in neuroinflammation, metabolism and behavior. The predatory stress model, a model showing the effects of stress on brain inflammation in mice, may be useful in elucidating mechanisms by which psychological stress modulates diseases with an inflammatory component (Barnum, C. J., Pace, T. W., Hu, F. et al. J Neuroinflammation (2012) 9: 9).

Metabolomics studies predict the impact of an obesogenic diet and stress on insulin resistance (E. Barone et al./Free Radical Biology and Medicine 91 (2016) 127-142).

The specific causes of insulin resistance and other complications related to acute or chronic insulin impairment may vary among individuals and remains largely unsolved.

Mounting evidence suggests that obesity induces metabolic and immune responses in the gut-liver-brain axis that lead to increased risk of insulin resistance and central nervous system (CNS) alterations. Tumor Necrosis Factor (TNF) signaling is implicated in type-2 diabetes (T2D) onset and progression and TNF-dependent pathways may be critical mediators of the metabolic dysregulation inherent in obesity.

SUMMARY OF INVENTION

It has been discovered that solTNF neutralization ameliorates insulin resistance and metabolic, immune, and behavioral phenotypes in diet-induced obesity (DIO). In experiments, C57Bl/6J male mice received high-fat, high-carbohydrate (HFHC) diet for 14 weeks. A selective inhibitor of solTNF, XPRO1595, was used to block solTNF-dependent pathways. Behavioral, metabolic, and immune alterations were evaluated in the gut-liver-brain axis. Metabolomics analysis was used to assess metabolic dysregulation. We found that HFHC diet promoted alterations of nucleotides and lipids and a metabolic inflammatory profile associated with hepatic steatosis and insulin dysregulation. HFHC diet disrupted insulin signaling in the prefrontal cortex, hypothalamus, and liver. XPRO1595 decreased circulating insulin levels and prostaglandin, tryptophan and cholesterol metabolites. Additionally, solTNF neutralization decreased hepatic and colonic lipocalin-2—an inflammatory marker associated with insulin resistance, hepatic steatosis and intestinal inflammation. HFHC diet consumption can affect a number of metabolic pathways that involve the brain-gut-liver axis and promote insulin impairment and peripheral inflammation. Inhibition of solTNF can partially revert deleterious central and peripheral metabolic, inflammatory, and behavioral outcomes present in DIO. Accordingly, it has been surprisingly discovered that selective inhibition of solTNF improves insulin sensitivity and reduces the impact of a HFHC diet on the brain-gut-liver axis components.

In accordance with these findings, herein disclosed is a method for treating complications related to acute or chronic insulin resistance, the method comprising: (i) determining a level of lipocalin-2 (LCN2) in a patient; and (ii) if the level of LCN2 is greater than a predetermined-value, administering to the patient a therapeutically effective amount of a selective inhibitor of soluble tumor necrosis factor (solTNF), whereby said complications are treated.

Other particulars and variations are described in the description of embodiments and the drawings appended hereto.

BRIEF DESCRIPTION OF DRAWINGS

FIG. 1A shows the nucleic acid sequence of human TNF-α (SEQ ID NO:1). An additional six histidine codons, located between the start codon and the first amino acid, are underlined.

FIG. 1B shows the amino acid sequence of human TNF-α (SEQ ID NO:2) with an additional 6 histidines (underlined) between the start codon and the first amino acid. Amino acids changed in exemplary TNF-α variants are shown in bold.

FIG. 1C shows the amino acid sequence of human TNF-α (SEQ ID NO:3).

FIG. 2 shows the positions and amino acid changes in certain TNF-α variants.

DESCRIPTION OF EMBODIMENTS

Figure 3A:
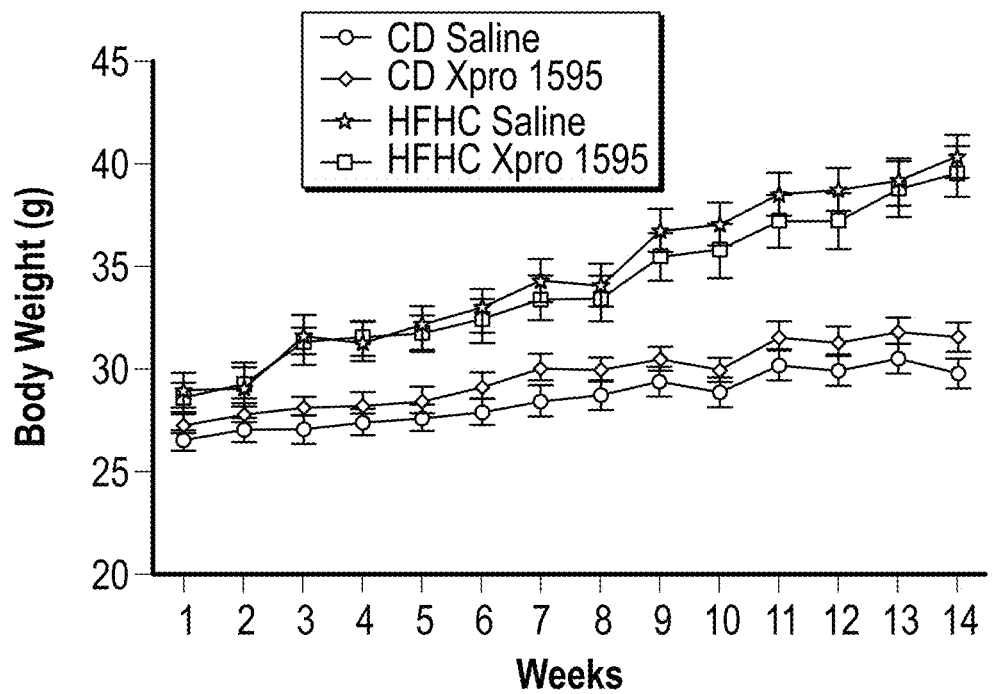
FIG. 3A shows a plot associated with a DIO rodent model indicating increased body weight over a period of 14 weeks.

Disclosed herein is the novel and unexpected finding that selective inhibition of soluble TNF-α can be used to ameliorate insulin resistance and other complications associated with acute or chronic hyperglycemia, and/or diet induced obesity, specifically those complications characterized by or associated with an elevated level of lipocalin-2 (LCN2).

Selective Inhibitors of Soluble Tumor Necrosis Factor

Proteins with TNF-α antagonist activity, and nucleic acids encoding these proteins, were previously discovered which function to inhibit the soluble form of TNF-α (solTNF) without inhibiting transmembrane TNF-α (tmTNF); collectively these proteins and nucleic acids encoding these proteins are herein collectively referred to as "selective inhibitors of solTNF".

Examples of selective inhibitors of solTNF are disclosed in U.S. Pat. Nos. 7,056,695; 7,101,974; 7,144,987; 7,244,823; 7,446,174; 7,662,367; and 7,687,461; the entire contents of each of which is hereby incorporated by reference.

Preferred selective inhibitors of solTNF may be dominant negative TNFα proteins, referred to herein as "DNTNF-α," "DN-TNF-α proteins," "TNFα variants," "TNFα variant proteins," "variant TNF-α," "variant TNF-α," and the like. By "variant TNF-α" or "TNF-α proteins" is meant TNFα or TNF-α proteins that differ from the corresponding wild type protein by at least 1 amino acid. Thus, a variant of human TNF-α is compared to SEQ ID NO:1 (nucleic acid including codons for 6 histidines), SEQ ID NO:2 (amino acid including 6 N-terminal histidines) or SEQ ID NO:3 (amino acid without 6 N-terminal histidines). DN-TNF-α proteins are disclosed in detail in U.S. Pat. No. 7,446,174, which is incorporated herein in its entirety by reference. As used herein variant TNF-α or TNF-α proteins include TNF-α monomers, dimers or trimers. Included within the definition of "variant TNF-α" are competitive inhibitor TNF-α variants. While certain variants as described herein, one of skill in the art will understand that other variants may be made while retaining the function of inhibiting soluble but not transmembrane TNF-α.

Thus, the proteins of the invention are antagonists of wild type TNF-α. By "antagonists of wild type TNF-α" is meant that the variant TNF-α protein inhibits or significantly decreases at least one biological activity of wild-type TNF-α.

In a preferred embodiment the variant is antagonist of soluble TNF-α, but does not significantly antagonize transmembrane TNF-α, e.g., DN-TNF-α protein as disclosed herein inhibits signaling by soluble TNF-α, but not transmembrane TNF-α. By "inhibits the activity of TNF-α" and grammatical equivalents is meant at least a 10% reduction in wild-type, soluble TNF-α, more preferably at least a 50% reduction in wild-type, soluble TNF-α activity, and even more preferably, at least 90% reduction in wild-type, soluble TNF-α activity. Preferably there is an inhibition in wild-type soluble TNF-α activity in the absence of reduced signaling by transmembrane TNF-α. In a preferred embodiment, the activity of soluble TNF-α is inhibited while the activity of transmembrane TNF-α is substantially and preferably completely maintained.

The TNF proteins useful in various embodiments of the invention have modulated activity as compared to wild type proteins. In a preferred embodiment, variant TNF-α proteins exhibit decreased biological activity (e.g. antagonism) as compared to wild type TNF-α, including but not limited to, decreased binding to a receptor (p55, p75 or both), decreased activation and/or ultimately a loss of cytotoxic activity. By "cytotoxic activity" herein refers to the ability of a TNF-α variant to selectively kill or inhibit cells. Variant TNF-α proteins that exhibit less than 50% biological activity as compared to wild type are preferred. More preferred are variant TNF-α proteins that exhibit less than 25%, even more preferred are variant proteins that exhibit less than 15%, and most preferred are variant TNF-α proteins that exhibit less than 10% of a biological activity of wild-type TNF-α. Suitable assays include, but are not limited to, caspase assays, TNF-α cytotoxicity assays, DNA binding assays, transcription assays (using reporter constructs), size exclusion chromatography assays and radiolabeling/immuno-precipitation,), and stability assays (including the use of circular dichroism (CD) assays and equilibrium studies), according to methods know in the art.

In one embodiment, at least one property critical for binding affinity of the variant TNF-α proteins is altered when compared to the same property of wild type TNF-α and in particular, variant TNF-α proteins with altered receptor affinity are preferred. Particularly preferred are variant TNF-α with altered affinity toward oligomerization to wild type TNF-α. Thus, the invention makes use of variant TNF-α proteins with altered binding affinities such that the variant TNF-α proteins will preferentially oligomerize with wild type TNF-α, but do not substantially interact with wild type TNF receptors, i.e., p55, p75. "Preferentially" in this case means that given equal amounts of variant TNF-α monomers and wild type TNF-α monomers, at least 25% of the resulting trimers are mixed trimers of variant and wild type TNF-α, with at least about 50% being preferred, and at least about 80-90% being particularly preferred. In other words, it is preferable that the variant TNF-α proteins implemented in embodiments of the invention have greater affinity for wild type TNF-α protein as compared to wild type TNF-α proteins. By "do not substantially interact with TNF receptors" is meant that the variant TNF-α proteins will not be able to associate with either the p55 or p75 receptors to significantly activate the receptor and initiate the TNF signaling pathway(s). In a preferred embodiment, at least a 50% decrease in receptor activation is seen, with greater than 50%, 75%, 80-90% being preferred.

In some embodiments, the variants of the invention are antagonists of both soluble and transmembrane TNF-α. However, as described herein, preferred variant TNF-α proteins are antagonists of the activity of soluble TNF-α but do not substantially affect the activity of transmembrane TNF-α. Thus, a reduction of activity of the heterotrimers for soluble TNF-α is as outlined above, with reductions in biological activity of at least 10%, 25, 50, 75, 80, 90, 95, 99 or 100% all being preferred. However, some of the variants outlined herein comprise selective inhibition; that is, they inhibit soluble TNF-α activity but do not substantially inhibit transmembrane TNF-α. In these embodiments, it is preferred that at least 80%, 85, 90, 95, 98, 99 or 100% of the transmembrane TNF-α activity is maintained. This may also be expressed as a ratio; that is, selective inhibition can include a ratio of inhibition of soluble to transmembrane TNF-α. For example, variants that result in at least a 10:1 selective inhibition of soluble to transmembrane TNF-α activity are preferred, with 50:1, 100:1, 200:1, 500:1, 1000:1 or higher find particular use in the invention. Thus, one embodiment utilizes variants, such as double mutants at positions 87/145 as outlined herein, that substantially inhibit or eliminate soluble TNF-α activity (for example by exchanging with homotrimeric wild-type to form heterotrimers that do not bind to TNF-α receptors or that bind but do not activate receptor signaling) but do not significantly affect (and preferably do not alter at all) transmembrane TNF-α activity. Without being bound by theory, the variants exhibiting such differential inhibition allow the decrease of inflammation without a corresponding loss in immune response.

In one embodiment, the affected biological activity of the variants is the activation of receptor signaling by wild type TNF-α proteins. In a preferred embodiment, the variant TNF-α protein interacts with the wild type TNF-α protein such that the complex comprising the variant TNF-α and wild type TNF-α has reduced capacity to activate (as outlined above for "substantial inhibition"), and in preferred embodiments is incapable of activating, one or both of the TNF receptors, i.e. p55 TNF-R or p75 TNF-R. In a preferred embodiment, the variant TNF-α protein is a variant TNF-α protein that functions as an antagonist of wild type TNF-α. Preferably, the variant TNF-α protein preferentially interacts with wild type TNF-α to form mixed trimers with the wild type protein such that receptor binding does not significantly occur and/or TNF-α signaling is not initiated. By mixed trimers is meant that monomers of wild type and variant TNF-α proteins interact to form heterotrimeric TNF-α. Mixed trimers may comprise 1 variant TNF-α protein:2 wild type TNF-α proteins, 2 variant TNF-α proteins:1 wild type TNF-α protein. In some embodiments, trimers may be formed comprising only variant TNF-α proteins.

The variant TNF-α antagonist proteins implemented in embodiments of the invention are highly specific for TNF-α antagonism relative to TNF-beta antagonism. Additional characteristics include improved stability, pharmacokinetics, and high affinity for wild type TNF-α. Variants with higher affinity toward wild type TNF-α may be generated from variants exhibiting TNF-α antagonism as outlined above.

Similarly, variant TNF-α proteins, for example are experimentally tested and validated in in vivo and in in vitro assays. Suitable assays include, but are not limited to, activity assays and binding assays. For example, TNF-α activity assays, such as detecting apoptosis via caspase activity can be used to screen for TNF-α variants that are antagonists of wild type TNF-α. Other assays include using the Sytox green nucleic acid stain to detect TNF-induced cell permeability in an Actinomycin-D sensitized cell line. As this stain is excluded from live cells, but penetrates dying cells, this assay also can be used to detect TNF-α variants that are agonists of wild-type TNF-α. By "agonists of wild type TNF-α" is meant that the variant TNF-α protein enhances the activation of receptor signaling by wild type TNF-α proteins. Generally, variant TNF-α proteins that function as agonists of wild type TNF-α are not preferred. However, in some embodiments, variant TNF-α proteins that function as agonists of wild type TNF-α protein are preferred. An example of an NF kappaB assay is presented in Example 7 of U.S. Pat. No. 7,446,174, which is expressly incorporated herein by reference.

In a preferred embodiment, binding affinities of variant TNF-α proteins as compared to wild type TNF-α proteins for naturally occurring TNF-α and TNF receptor proteins such as p55 and p75 are determined. Suitable assays include, but are not limited to, e.g., quantitative comparisons comparing kinetic and equilibrium binding constants, as are known in the art. Examples of binding assays are described in Example 6 of U.S. Pat. No. 7,446,174, which is expressly incorporated herein by reference.

In a preferred embodiment, the variant TNF-α protein has an amino acid sequence that differs from a wild type TNF-α sequence by at least 1 amino acid, with from 1, 2, 3, 4, 5, 6, 7, 8, 9 and 10 amino acids all contemplated, or higher. Expressed as a percentage, the variant TNF-α proteins of the invention preferably are greater than 90% identical to wild-type, with greater than 95, 97, 98 and 99% all being contemplated. Stated differently, based on the human TNF-α sequence of FIG. 1B (SEQ ID NO:2) excluding the N-terminal 6 histidines, as shown in FIG. 1C (SEQ ID NO:3), variant TNF-α proteins have at least about 1 residue that differs from the human TNF-α sequence, with at least about 2, 3, 4, 5, 6, 7 or 8 different residues. Preferred variant TNF-α proteins have 3 to 8 different residues.

A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored). In a similar manner, "percent (%) nucleic acid sequence identity" with respect to the coding sequence of the polypeptides identified is defined as the percentage of nucleotide residues in a candidate sequence that are identical with the nucleotide residues in the coding sequence of the cell cycle protein. A preferred method utilizes the BLASTN module of WU-BLAST-2 set to the default parameters, with overlap span and overlap fraction set to 1 and 0.125, respectively.

TNF-α proteins may be fused to, for example, other therapeutic proteins or to other proteins such as Fc or serum albumin for therapeutic or pharmacokinetic purposes. In this embodiment, a TNF-α protein implemented in embodiments of the invention is operably linked to a fusion partner. The fusion partner may be any moiety that provides an intended therapeutic or pharmacokinetic effect. Examples of fusion partners include but are not limited to Human Serum Albumin, a therapeutic agent, a cytotoxic or cytotoxic molecule, radionucleotide, and an Fc, etc. As used herein, an Fc fusion is synonymous with the terms "immunoadhesin", "Ig fusion", "Ig chimera", and "receptor globulin" as used in the prior art (Chamow et al., 1996, Trends Biotechnol 14:52-60; Ashkenazi et al., 1997, Curr Opin Immunol 9:195-200, both incorporated by reference). An Fc fusion combines the Fc region of an immunoglobulin with the target-binding region of a TNF-α protein, for example. See for example U.S. Pat. Nos. 5,766,883 and 5,876,969, both of which are hereby incorporated by reference.

In a preferred embodiment, the variant TNF-α proteins comprise variant residues selected from the following positions 21, 23, 30, 31, 32, 33, 34, 35, 57, 65, 66, 67, 69, 75, 84, 86, 87, 91, 97, 101, 111, 112, 115, 140, 143, 144, 145, 146, and 147. Preferred amino acids for each position, including the human TNF-α residues, are shown in FIG. 2. Thus, for example, at position 143, preferred amino acids are Glu, Asn, Gln, Ser, Arg, and Lys; etc. Preferred changes include: V1M, Q21C, Q21 R, E23C, R31C, N34E, V91E, Q21R, N30D, R31C, R31I, R31D, R31E, R32D, R32E, R32S, A33E, N34E, N34V, A35S, D45C, L57F, L57W, L57Y, K65D, K65E, K65I, K65M, K65N, K65Q, K65T, K65S, K65V, K65W, G66K, G66Q, Q67D, Q67K, Q67R, Q67S, Q67W, Q67Y, C69V, L75E, L75K, L75Q, A84V, S86Q, S86R, Y87H, Y87R, V91E, I97R, I97T, C101A, A111R, A111E, K112D, K112E, Y115D, Y115E, Y115F, Y115H, Y115I, Y115K, Y115L, Y115M, Y115N, Y115Q, Y115R, Y115S, Y115T, Y115W, D140K, D140R, D143E, D143K, D143L, D143R, D143N, D143Q, D143R, D143S, F144N, A145D, A145E, A145F, A145H, A145K, A145M, A145N, A145Q, A145R, A145S, A145T, A145Y, E146K, E146L, E146M, E146N, E146R, E146S and S147R. These may be done either individually or in combination, with any combination being possible. However, as outlined herein, preferred embodiments utilize at least 1 to 8, and preferably more, positions in each variant TNF-α protein.

In an additional aspect, the invention provides TNF-α variants selected from the group consisting of XENP268 XENP344, XENP345, XENP346, XENP550, XENP551, XENP557, XENP1593, XENP1594, and XENP1595 as outlined in Example 3 OF U.S. Pat. No. 7,662,367, which is incorporated herein by reference.

In an additional aspect, the invention makes use of methods of forming a TNF-α heterotrimer in vivo in a mammal comprising administering to the mammal a variant TNF-α molecule as compared to the corresponding wild-type mammalian TNF-α, wherein said TNF-α variant is substantially free of agonistic activity.

In an additional aspect, the invention makes use of methods of screening for selective inhibitors comprising contacting a candidate agent with a soluble TNF-α protein and assaying for TNF-α biological activity; contacting a candidate agent with a transmembrane TNF-α protein and assaying for TNF-α biological activity, and determining whether the agent is a selective inhibitor. The agent may be a protein (including peptides and antibodies, as described herein) or small molecules.

In a further aspect, the invention makes use of variant TNF-α proteins that interact with the wild type TNF-α to form mixed trimers incapable of activating receptor signaling. Preferably, variant TNF-α proteins with 1, 2, 3, 4, 5, 6 and 7 amino acid changes are used as compared to wild type TNF-α protein. In a preferred embodiment, these changes are selected from positions 1, 21, 23, 30, 31, 32, 33, 34, 35, 57, 65, 66, 67, 69, 75, 84, 86, 87, 91, 97, 101, 111, 112, 115, 140, 143, 144, 145, 146 and 147. In an additional aspect, the non-naturally occurring variant TNF-α proteins have substitutions selected from the group of substitutions consisting of: V1M, Q21C, Q21R, E23C, N34E, V91E, Q21R, N30D, R31C, R31I, R31D, R31E, R32D, R32E, R32S, A33E, N34E, N34V, A35S, D45C, L57F, L57W, L57Y, K65D, K65E, K65I, K65M, K65N, K65Q, K65T, K65S, K65V, K65W, G66K, G66Q, Q67D, Q67K, Q67R, Q67S, Q67W, Q67Y, C69V, L75E, L75K, L75Q, A84V, S86Q, S86R, Y87H, Y87R, V91E, I97R, I97T, C101A, A111R, A111E, K112D, K112E, Y115D, Y115E, Y115F, Y115H, Y115I, Y115K, Y115L, Y115M, Y115N, Y115Q, Y115R, Y115S, Y115T, Y115W, D140K, D140R, D143E, D143K, D143L, D143R, D143N, D143Q, D143R, D143S, F144N, A145D, A145E, A145F, A145H, A145K, A145M, A145N, A145Q, A145R, A145S, A145T, A145Y, E146K, E146L, E146M, E146N, E146R, E146S and S147R.

In another preferred embodiment, substitutions may be made either individually or in combination, with any combination being possible. Preferred embodiments utilize at least one, and preferably more, positions in each variant TNF-α protein. For example, substitutions at positions 31, 57, 69, 75, 86, 87, 97, 101, 115, 143, 145, and 146 may be combined to form double variants. In addition, triple, quadruple, quintuple and the like, point variants may be generated.

In one aspect the invention makes use of TNF-α variants comprising the amino acid substitutions A145R/I97T. In one aspect, the invention provides TNF-α variants comprising the amino acid substitutions V1M, R31C, C69V, Y87H, C101A, and A145R. In a preferred embodiment, this variant is PEGylated.

In a preferred embodiment the variant is XPRO1595, a PEGylated protein comprising VIM, R31C, C69V, Y87H, C101A, and A145R mutations relative to the wild type human sequence, also referred to herein as "XPro".

For purposes of the present invention, the areas of the wild type or naturally occurring TNF-α molecule to be modified are selected from the group consisting of the Large Domain (also known as II), Small Domain (also known as I), the DE loop, and the trimer interface. The Large Domain, the Small Domain and the DE loop are the receptor interaction domains. The modifications may be made solely in one of these areas or in any combination of these areas. The Large Domain preferred positions to be varied include: 21, 30, 31, 32, 33, 35, 65, 66, 67, 111, 112, 115, 140, 143, 144, 145, 146 and/or 147. For the Small Domain, the preferred positions to be modified are 75 and/or 97. For the DE Loop, the preferred position modifications are 84, 86, 87 and/or 91. The Trimer Interface has preferred double variants including positions 34 and 91 as well as at position 57. In a preferred embodiment, substitutions at multiple receptor interaction and/or trimerization domains may be combined. Examples include, but are not limited to, simultaneous substitution of amino acids at the large and small domains (e.g. A145R and I97T), large domain and DE loop (A145R and Y87H), and large domain and trimerization domain (A145R and L57F). Additional examples include any and all combinations, e.g., I97T and Y87H (small domain and DE loop). More specifically, theses variants may be in the form of single point variants, for example K112D, Y115K, Y115I, Y115T, A145E or A145R. These single point variants may be combined, for example, Y115I and A145E, or Y115I and A145R, or Y115T and A145R or Y115I and A145E; or any other combination.

Preferred double point variant positions include 57, 75, 86, 87, 97, 115, 143, 145, and 146; in any combination. In addition, double point variants may be generated including L57F and one of Y115I, Y115Q, Y115T, D143K, D143R, D143E, A145E, A145R, E146K or E146R. Other preferred double variants are Y115Q and at least one of D143N, D143Q, A145K, A145R, or E146K; Y115M and at least one of D143N, D143Q, A145K, A145R or E146K; and L57F and at least one of A145E or 146R; K65D and either D143K or D143R, K65E and either D143K or D143R, Y115Q and any of L75Q, L57W, L57Y, L57F, I97R, I97T, S86Q, D143N, E146K, A145R and I97T, A145R and either Y87R or Y87H; N34E and V91E; L75E and Y115Q; L75Q and Y115Q; L75E and A145R; and L75Q and A145R.

Further, triple point variants may be generated. Preferred positions include 34, 75, 87, 91, 115, 143, 145 and 146. Examples of triple point variants include V91 E, N34E and one of Y115I, Y115T, D143K, D143R, A145R, A145E E146K, and E146R. Other triple point variants include L75E and Y87H and at least one of Y115Q, A145R, Also, L75K, Y87H and Y115Q. More preferred are the triple point variants V91E, N34E and either A145R or A145E.

Variant TNF-α proteins may also be identified as being encoded by variant TNF-α nucleic acids. In the case of the nucleic acid, the overall homology of the nucleic acid sequence is commensurate with amino acid homology but takes into account the degeneracy in the genetic code and codon bias of different organisms. Accordingly, the nucleic acid sequence homology may be either lower or higher than that of the protein sequence, with lower homology being preferred. In a preferred embodiment, a variant TNF-α nucleic acid encodes a variant TNF-α protein. As will be appreciated by those in the art, due to the degeneracy of the genetic code, an extremely large number of nucleic acids may be made, all of which encode the variant TNF-α proteins of the present invention. Thus, having identified a particular amino acid sequence, those skilled in the art could make any number of different nucleic acids, by simply modifying the sequence of one or more codons in a way which does not change the amino acid sequence of the variant TNF-α.

In one embodiment, the nucleic acid homology is determined through hybridization studies. Thus, for example, nucleic acids which hybridize under high stringency to the nucleic acid sequence shown in FIG. 1A (SEQ ID NO:1) or its complement and encode a variant TNF-α protein is considered a variant TNF-α gene. High stringency conditions are known in the art; see for example Maniatis et al., Molecular Cloning: A Laboratory Manual, 2d Edition, 1989, and Short Protocols in Molecular Biology, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993), incorporated by reference. Generally, stringent conditions are selected to be about 5-10° C. lower than the thermal melting point (Tm) for the specific sequence at a defined ionic strength and pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide. In another embodiment, less stringent hybridization conditions are used; for example, moderate or low stringency conditions may be used, as are known in the art; see Maniatis and Ausubel, supra, and Tij ssen, supra. In addition, nucleic acid variants encode TNF-α protein variants comprising the amino acid substitutions described herein. In one embodiment, the TNF-α variant encodes a polypeptide variant comprising the amino acid substitutions A145R/197T. In one aspect, the nucleic acid variant encodes a polypeptide comprising the amino acid substitutions V1M, R31C, C69V, Y87H, C101A, and A145R, or any 1, 2, 3, 4 or 5 of these variant amino acids.

The variant TNF-α proteins and nucleic acids of the present invention are recombinant. As used herein, "nucleic acid" may refer to either DNA or RNA, or molecules which contain both deoxy- and ribonucleotides. The nucleic acids include genomic DNA, cDNA and oligonucleotides including sense and anti-sense nucleic acids. Such nucleic acids may also contain modifications in the ribose-phosphate backbone to increase stability and half-life of such molecules in physiological environments. The nucleic acid may be double stranded, single stranded, or contain portions of both double stranded or single stranded sequence. As will be appreciated by those in the art, the depiction of a single strand ("Watson") also defines the sequence of the other strand ("Crick"); thus, the sequence depicted in FIG. 1A (SEQ ID NO:1) also includes the complement of the sequence. By the term "recombinant nucleic acid" is meant nucleic acid, originally formed in vitro, in general, by the manipulation of nucleic acid by endonucleases, in a form not normally found in nature. Thus, an isolated variant TNF-α nucleic acid, in a linear form, or an expression vector formed in vitro by ligating DNA molecules that are not normally joined, are both considered recombinant for the purposes of this invention.

By "vector" is meant any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors.

It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Similarly, a "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated or purified away from some or all of the proteins and compounds with which it is normally associated in its wild-type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of a variant TNF-α protein from one organism in a different organism or host cell. Alternatively, the protein may be made at a significantly higher concentration than is normally seen, through the use of an inducible promoter or high expression promoter, such that the protein is made at increased concentration levels. Furthermore, all of the variant TNF-α proteins outlined herein are in a form not normally found in nature, as they contain amino acid substitutions, insertions and deletions, with substitutions being preferred, as discussed below.

Also included within the definition of variant TNF-α proteins of the present invention are amino acid sequence variants of the variant TNF-α sequences outlined herein and shown in the Figures. That is, the variant TNF-α proteins may contain additional variable positions as compared to human TNF-α. These variants fall into one or more of three classes: substitutional, insertional or deletional variants.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Using the nucleic acids disclosed herein, which encode a variant TNF-α protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the variant TNF-α protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation.

In a preferred embodiment, when the endogenous secretory sequence leads to a low level of secretion of the naturally occurring protein or of the variant TNF-α protein, a replacement of the naturally occurring secretory leader sequence is desired. In this embodiment, an unrelated secretory leader sequence is operably linked to a variant TNF-α encoding nucleic acid leading to increased protein secretion. Thus, any secretory leader sequence resulting in enhanced secretion of the variant TNF-α protein, when compared to the secretion of TNF-α and its secretory sequence, is desired. Suitable secretory leader sequences that lead to the secretion of a protein are known in the art. In another preferred embodiment, a secretory leader sequence of a naturally occurring protein or a protein is removed by techniques known in the art and subsequent expression results in intracellular accumulation of the recombinant protein.

Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used to express the fusion protein; for example, transcriptional and translational regulatory nucleic acid sequences from *Bacillus* are preferably used to express the fusion protein in *Bacillus*. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences. Promoter sequences encode either constitutive or inducible promoters. The promoters may be either naturally occurring promoters or hybrid promoters. Hybrid promoters, which combine elements of more than one promoter, are also known in the art, and are useful in the present invention. In a preferred embodiment, the promoters are strong promoters, allowing high expression in cells, particularly mammalian cells, such as the CMV promoter, particularly in combination with a Tet regulatory element.

In addition, the expression vector may comprise additional elements. For example, the expression vector may have two replication systems, thus allowing it to be maintained in two organisms, for example in mammalian or insect cells for expression and in a prokaryotic host for cloning and amplification. Furthermore, for integrating expression vectors, the expression vector contains at least one sequence homologous to the host cell genome, and preferably two homologous sequences that flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used. A preferred expression vector system is a retroviral vector system such as is generally described in PCT/US97/01019 and PCT/US97/01048, both of which are hereby incorporated by reference. In a preferred embodiment, the expression vector comprises the components described above and a gene encoding a variant TNF-α protein. As will be appreciated by those in the art, all combinations are possible and accordingly, as used herein, the combination of components, comprised by one or more vectors, which may be retroviral or not, is referred to herein as a "vector composition".

A number of viral based vectors have been used for gene delivery. See for example U.S. Pat. No. 5,576,201, which is expressly incorporated herein by reference. For example, retroviral systems are known and generally employ packaging lines which have an integrated defective provirus (the "helper") that expresses all of the genes of the virus but cannot package its own genome due to a deletion of the packaging signal, known as the psi sequence. Thus, the cell line produces empty viral shells. Producer lines can be derived from the packaging lines which, in addition to the helper, contain a viral vector, which includes sequences required in cis for replication and packaging of the virus, known as the long terminal repeats (LTRs). The gene of interest can be inserted in the vector and packaged in the viral shells synthesized by the retroviral helper. The recombinant virus can then be isolated and delivered to a subject. (See, e.g., U.S. Pat. No. 5,219,740.) Representative retroviral vectors include but are not limited to vectors such as the LHL, N2, LNSAL, LSHL and LHL2 vectors described in e.g., U.S. Pat. No. 5,219,740, incorporated herein by reference in its entirety, as well as derivatives of these vectors. Retroviral vectors can be constructed using techniques well known in the art. See, e.g., U.S. Pat. No. 5,219,740; Mann et al. (1983) Cell 33:153-159.

Adenovirus based systems have been developed for gene delivery and are suitable for delivery according to the methods described herein. Human adenoviruses are double-stranded DNA viruses that enter cells by receptor-mediated endocytosis. These viruses are particularly well suited for gene transfer because they are easy to grow and manipulate and they exhibit a broad host range in vivo and in vitro.

Adenoviruses infect quiescent as well as replicating target cells. Unlike retroviruses which integrate into the host genome, adenoviruses persist extrachromosomally thus minimizing the risks associated with insertional mutagenesis. The virus is easily produced at high titers and is stable so that it can be purified and stored. Even in the replication-competent form, adenoviruses cause only low-level morbidity and are not associated with human malignancies. Accordingly, adenovirus vectors have been developed which make use of these advantages. For a description of adenovirus vectors and their uses see, e.g., Haj-Ahmad and Graham (1986) J. Virol. 57:267-274; Bett et al. (1993) J. Virol. 67:5911-5921; Mittereder et al. (1994) Human Gene Therapy 5:717-729; Seth et al. (1994) J. Virol. 68:933-940; Barr et al. (1994) Gene Therapy 1:51-58; Berkner, K. L. (1988) BioTechniques 6:616-629; Rich et al. (1993) Human Gene Therapy 4:461-476.

In a preferred embodiment, the viral vectors used in the subject methods are AAV vectors. By an "AAV vector" is meant a vector derived from an adeno-associated virus serotype, including without limitation, AAV-1, AAV-2, AAV- 3, AAV-4, AAV-5, AAVX7, etc. Typical AAV vectors can have one or more of the AAV wild-type genes deleted in whole or part, preferably the rep and/or cap genes, but retain functional flanking ITR sequences. Functional ITR sequences are necessary for the rescue, replication and packaging of the AAV virion. An AAV vector includes at least those sequences required in cis for replication and packaging (e.g., functional ITRs) of the virus. The ITRs need not be the wild-type nucleotide sequences, and may be altered, e.g., by the insertion, deletion or substitution of nucleotides, so long as the sequences provide for functional rescue, replication and packaging. For more on various AAV serotypes, see for example Cearley et al., Molecular Therapy, 16:1710-1718, 2008, which is expressly incorporated herein in its entirety by reference.

AAV expression vectors may be constructed using known techniques to provide as operatively linked components in the direction of transcription, control elements including a transcriptional initiation region, the DNA of interest and a transcriptional termination region. The control elements are selected to be functional in a thalamic and/or cortical neuron. Additional control elements may be included. The resulting construct, which contains the operatively linked components is bounded (5' and 3') with functional AAV ITR sequences.

By "adeno-associated virus inverted terminal repeats" or "AAV ITRs" is meant the art-recognized regions found at each end of the AAV genome which function together in cis as origins of DNA replication and as packaging signals for the virus. AAV ITRs, together with the AAV rep coding region, provide for the efficient excision and rescue from, and integration of a nucleotide sequence interposed between two flanking ITRs into a mammalian cell genome.

The nucleotide sequences of AAV ITR regions are known. See, e.g., Kotin, R. M. (1994) Human Gene Therapy 5:793-801; Berns, K. I. "Parvoviridae and their Replication" in Fundamental Virology, 2nd Edition, (B. N. Fields and D. M. Knipe, eds.) for the AAV-2 sequence. As used herein, an "AAV ITR" need not have the wild-type nucleotide sequence depicted, but may be altered, e.g., by the insertion, deletion or substitution of nucleotides. Additionally, the AAV ITR may be derived from any of several AAV serotypes, including without limitation, AAV-1, AAV-2, AAV-3, AAV-4, AAV-5, AAVX7, etc. Furthermore, 5' and 3' ITRs which flank a selected nucleotide sequence in an AAV vector need not necessarily be identical or derived from the same AAV serotype or isolate, so long as they function as intended, i.e., to allow for excision and rescue of the sequence of interest from a host cell genome or vector, and to allow integration of the heterologous sequence into the recipient cell genome when AAV Rep gene products are present in the cell.

Suitable DNA molecules for use in AAV vectors will include, for example, a gene that encodes a protein that is defective or missing from a recipient subject or a gene that encodes a protein having a desired biological or therapeutic effect (e.g., an enzyme, or a neurotrophic factor). The artisan of reasonable skill will be able to determine which factor is appropriate based on the neurological disorder being treated.

The selected nucleotide sequence is operably linked to control elements that direct the transcription or expression thereof in the subject in vivo. Such control elements can comprise control sequences normally associated with the selected gene. Alternatively, heterologous control sequences can be employed. Useful heterologous control sequences generally include those derived from sequences encoding mammalian or viral genes. Examples include, but are not limited to, the SV40 early promoter, mouse mammary tumor virus LTR promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, synthetic promoters, hybrid promoters, and the like. In addition, sequences derived from nonviral genes, such as the murine metallothionein gene, will also find use herein. Such promoter sequences are commercially available.

Once made, the TNF-α protein may be covalently modified. For instance, a preferred type of covalent modification of variant TNF-α comprises linking the variant TNF-α polypeptide to one of a variety of nonproteinaceous polymers, e.g., polyethylene glycol ("PEG"), polypropylene glycol, or polyoxyalkylenes, in the manner set forth in U.S. Pat. Nos. 4,640,835; 4,496,689; 4,301,144; 4,670,417; 4,791,192 or 4,179,337, incorporated by reference. These nonproteinaceous polymers may also be used to enhance the variant TNF-α's ability to disrupt receptor binding, and/or in vivo stability. In another preferred embodiment, cysteines are designed into variant or wild type TNF-α in order to incorporate (a) labeling sites for characterization and (b) incorporate PEGylation sites. For example, labels that may be used are well known in the art and include but are not limited to biotin, tag and fluorescent labels (e.g. fluorescein). These labels may be used in various assays as are also well known in the art to achieve characterization. A variety of coupling chemistries may be used to achieve PEGylation, as is well known in the art. Examples include but are not limited to, the technologies of Shearwater and Enzon, which allow modification at primary amines, including but not limited to, lysine groups and the N-terminus See, Kinstler et al, Advanced Drug Deliveries Reviews, 54, 477-485 (2002) and M J Roberts et al, Advanced Drug Delivery Reviews, 54, 459-476 (2002), both hereby incorporated by reference.

In one preferred embodiment, the optimal chemical modification sites are 21, 23, 31 and 45, taken alone or in any combination. In an even more preferred embodiment, a TNF-α variant of the present invention includes the R31C mutation.

In a preferred embodiment, the variant TNF-α protein is purified or isolated after expression. Variant TNF-α proteins may be isolated or purified in a variety of ways known to those skilled in the art depending on what other components are present in the sample.

In another preferred embodiment, the TNF-α protein is administered via gene modified autologous or allogeneic cellular therapy, wherein the gene therapy comprises mesenchymal stem cells expressing a construct of the TNF-α protein, preferably a DN-TNF-α protein, more preferably XPRO1595.

Complications of Acute and/or Chronic Hyperglycemia

As disclosed herein, when administered peripherally, selective inhibitors of solTNF, specifically DN-TNF-α proteins, and more specifically XPRO1595, may reduce systemic insulin resistance and metabolic and inflammatory alterations in the gut-liver-brain axis, and reduces lipocalin-2, and thus, may be used to treat complications of acute or chronic hyperglycemia and/or diet induced obesity (DIO), particularly those characterized by elevated lipocalin-2 (LCN2) in a patient.

In one embodiment, the complication related to acute or chronic hyperglycemia is any disorder characterized by elevated LCN-2, and can include complications such as diabetes mellitus, insulin resistance, hepatic steatosis; non-alcoholic hepatic steatosis; fibrotic liver disease, including cirrhosis secondary to chronic inflammatory disease; and vascular disease; and intestinal inflammation.

Treatment Methods

The terms "treatment", "treating", and the like, as used herein include amelioration or elimination of a disease or condition once it has been established or alleviation of the characteristic symptoms of such disease or condition. A method as disclosed herein may also be used to, depending on the condition of the patient, prevent the onset of a disease or condition or of symptoms associated with a disease or condition, including reducing the severity of a disease or condition or symptoms associated therewith prior to affliction with said disease or condition. Such prevention or reduction prior to affliction refers to administration of the compound or composition as described herein to a patient that is not at the time of administration afflicted with the disease or condition. "Preventing" also encompasses preventing the recurrence or relapse-prevention of a disease or condition or of symptoms associated therewith, for instance after a period of improvement.

Figure 10A:
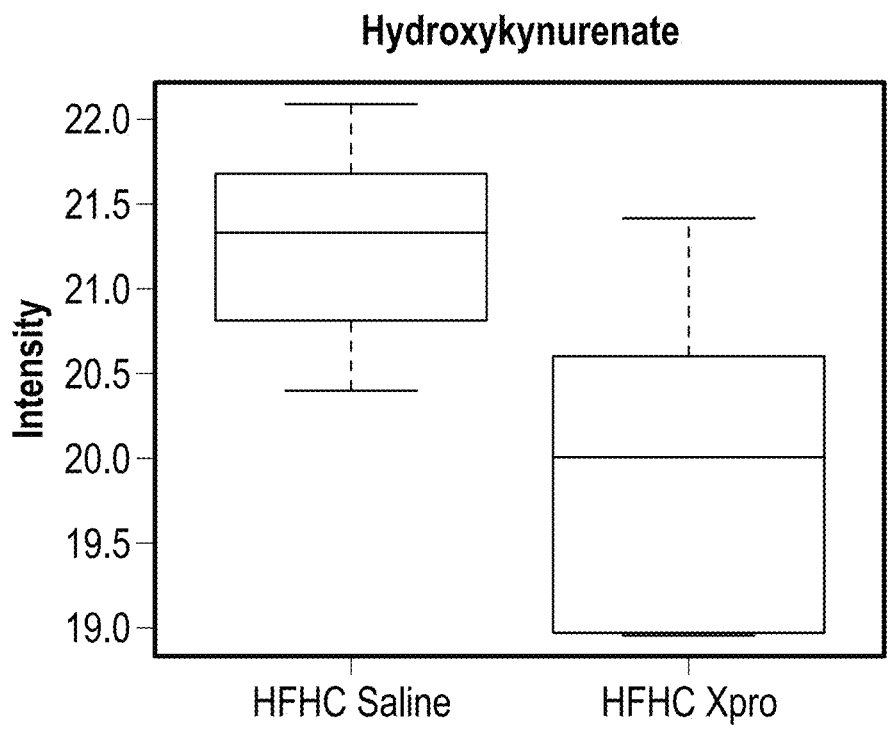
FIGS. 10(A-C) show pathway changes occurring with solTNF blocking include a decrease in cholesterol products and tryptophan and inflammatory metabolites
Figure 10B:
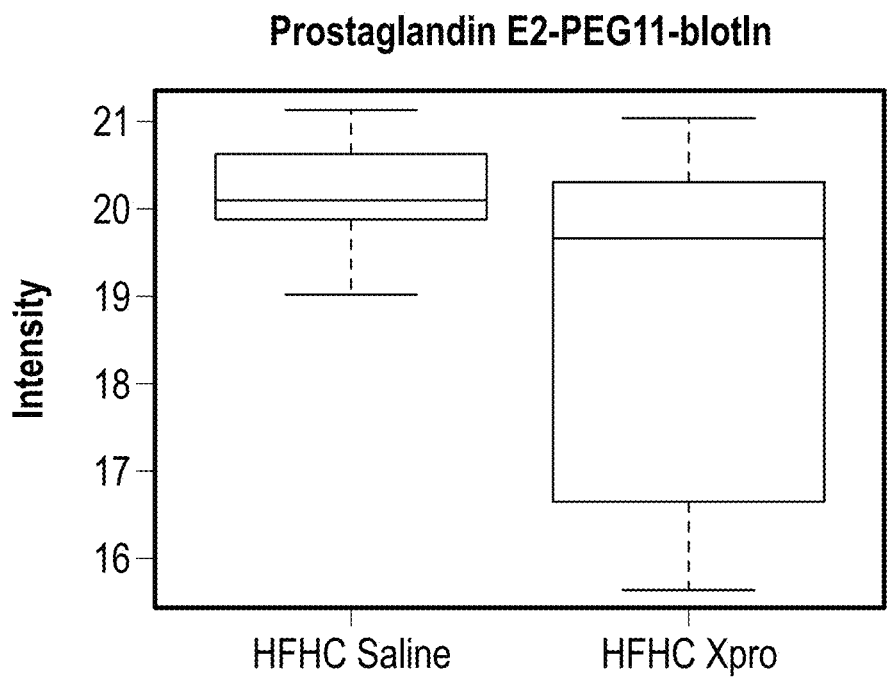
Figure 10C:
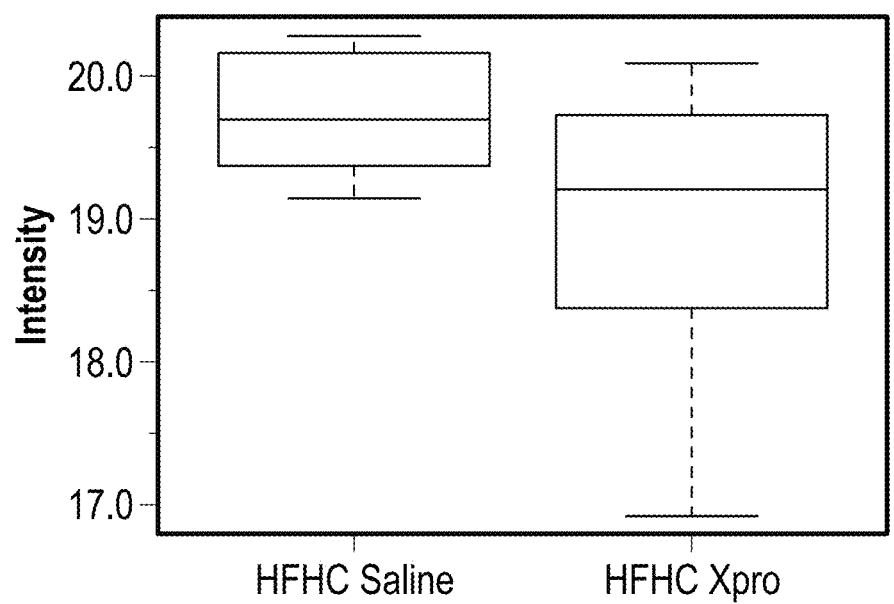

In one embodiment, a selective inhibitor of solTNF as described herein is administered peripherally to a patient in need thereof to reduce inflammation and/or reduce lipocalin-2 (LCN2). In another embodiment, a selective inhibitor of solTNF as described herein is administered peripherally to a patient in need thereof to decrease insulin and LCN2 plasma levels in a patient with diet-induced metabolic inflammation. In another embodiment, a selective inhibitor of solTNF as described herein is administered peripherally to a patient in need thereof to decrease colonic LCN2 and tight junction protein alterations associated with a high-fat, high-carbohydrate (HFHC) diet. In another embodiment, a selective inhibitor of solTNF as described herein is administered peripherally to a patient in need thereof to reduce hepatic LCN2 levels in the presence of diet-induced liver inflammation. In another embodiment, peripheral administration of a selective inhibitor of solTNF as described herein results in reduced inflammation in the gut-liver-brain axis. Peripheral administration of a selective inhibitor of solTNF as described herein can also ameliorate the effects of metabolic inflammation in the gut-liver-brain axis, for instance, XPro reduces the levels of a cholesterol metabolite that is processed in the liver and has brain effects (FIG. 10C).

In one embodiment, the treatment method includes administering a selective inhibitor of solTNF as described herein to a patient suffering from complications related to acute or chronic hyperglycemia and/or diet-induced obesity. Once treated, the patient may be monitored for improvements by measuring a number of biomarkers, including levels of C-reactive protein which may be measured according to methods known in the art as an indication of inflammation.

In one embodiment, the methods comprise peripheral administration of the selective inhibitor of solTNF for treatment of complications related to acute or chronic hyperglycemia and/or diet-induced obesity, such as diabetes mellitus, insulin resistance, hepatic steatosis; non-alcoholic hepatic steatosis; fibrotic liver disease, including cirrhosis secondary to chronic inflammatory disease; and vascular disease, and intestinal inflammation. By peripheral administration is meant administration to the circulation of a patient, e.g. delivery by injection or other delivery to the patient in a peripheral manner.

In an alternative embodiment the method comprises topical administration of a selective inhibitor of solTNF as described herein. In this embodiment the DN-TNF may be formulated as a lotion or cream.

Determining a Level of Lipocalin-2 (LCN2)

LCN2 can be measured using conventional assays known to one with the ordinary level of skill in the art, including assays for determining a level of LCN2 in urine (urine-derived LCN2 level), serum (serum-derived LCN2 level), plasma (plasma-derived LCN2 level), feces (feces derived LCN2 level), and saliva (saliva-derived LCN2 level).

While data fluctuates due heterogeneity in control groups (e.g. differences in gender, age, weight, etc.), it is generally appreciated that normal urine-derived LCN2 level in humans is in about 10.0-20.0 ng/mL; normal serum-derived LCN2 level in humans is about 100.0-140.0 ng/mL; normal plasma-derived LCN2 level in humans is about 70.0-110.0ng/mL; and normal saliva-derived LCN2 level in humans is about 100.0-500.0 ng/mL.

With these ranges in mind, we propose that in one embodiment "elevated LCN2" is any value above the upper end of these ranges. Therefore, for purposes herein, an "elevated LCN2 level" in humans is any value above: (i) 20 ng/mL (urine-derived LCN2 level); (ii) 140 ng/mL (serum-derived LCN2 level); (iii) 110.0 ng/mL (plasma-derived LCN2 level), and (iv) 500 ng/mL (saliva-derived LCN2 level). It should be recognized that other embodiments may be practiced outside of these ranges in accordance with generally accepted pre-determined thresholds for elevated LCN2.

Formulations

Depending upon the manner of introduction, the pharmaceutical composition may be formulated in a variety of ways. The concentration of the therapeutically active variant TNF-α protein in the formulation may vary from about 0.1 to 100 weight %. In another preferred embodiment, the concentration of the variant TNF-α protein is in the range of 0.003 to 1.0 molar, with dosages from 0.03, 0.05, 0.1, 0.2, and 0.3 millimoles per kilogram of body weight being preferred.

The pharmaceutical compositions for use in embodiments of the present invention comprise a variant TNF-α protein in a form suitable for administration to a patient. In the preferred embodiment, the pharmaceutical compositions are in a water-soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following: carrier proteins such as serum albumin; buffers such as NaOAc; fillers such as microcrystalline cellulose, lactose, corn and other starches; binding agents; sweeteners and other flavoring agents; coloring agents; and polyethylene glycol. Additives are well known in the art, and are used in a variety of formulations. In a further embodiment, the variant TNF-α proteins are added in a micellular formulation; see U.S. Pat. No. 5,833,948, hereby incorporated by reference. Alternatively, liposomes may be employed with the TNF-α proteins to effectively deliver the protein. Combinations of pharmaceutical compositions may be administered. Moreover, the TNF-α compositions of the present invention may be administered in combination with other therapeutics, either substantially simultaneously or co-administered, or serially, as the need may be.

In one embodiment provided herein, antibodies, including but not limited to monoclonal and polyclonal antibodies, are raised against variant TNF-α proteins using methods known in the art. In a preferred embodiment, these anti-variant TNF-α antibodies are used for immunotherapy. Thus, methods of immunotherapy are provided. By "immunotherapy" is meant treatment of TNF-α related disorders with an antibody raised against a variant TNF-α protein. As used herein, immunotherapy can be passive or active. Passive immunotherapy, as defined herein, is the passive transfer of antibody to a recipient (patient). Active immunization is the induction of antibody and/or T-cell responses in a recipient (patient). Induction of an immune response can be the consequence of providing the recipient with a variant TNF-α protein antigen to which antibodies are raised. As appreciated by one of ordinary skill in the art, the variant TNF-α protein antigen may be provided by injecting a variant TNF-α polypeptide against which antibodies are desired to be raised into a recipient, or contacting the recipient with a variant TNF-α protein encoding nucleic acid, capable of expressing the variant TNF-α protein antigen, under conditions for expression of the variant TNF-α protein antigen.

In another preferred embodiment, a therapeutic compound is conjugated to an antibody, preferably an anti-variant TNF-α protein antibody. The therapeutic compound may be a cytotoxic agent. Cytotoxic agents are numerous and varied and include, but are not limited to, cytotoxic drugs or toxins or active fragments of such toxins. Suitable toxins and their corresponding fragments include diphtheria A chain, exotoxin A chain, ricin A chain, abrin A chain, curcin, crotin, phenomycin, enomycin and the like. Cytotoxic agents also include radiochemicals made by conjugating radioisotopes to antibodies raised against cell cycle proteins, or binding of a radionuclide to a chelating agent that has been covalently attached to the antibody.

In a preferred embodiment, variant TNF-α proteins are administered as therapeutic agents, and can be formulated as outlined above. Similarly, variant TNF-α genes (including both the full-length sequence, partial sequences, or regulatory sequences of the variant TNF-α coding regions) may be administered in gene therapy applications, as is known in the art. These variant TNF-α genes can include antisense applications, either as gene therapy (i.e. for incorporation into the genome) or as antisense compositions, as will be appreciated by those in the art.

In a preferred embodiment, the nucleic acid encoding the variant TNF-α proteins may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., Proc. Natl. Acad. Sci. U.S.A. 83:4143-4146 (1986), incorporated by reference). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., Trends in Biotechnology 11:205-210 (1993), incorporated by reference). In some situations, it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., J. Biol. Chem. 262:4429-4432 (1987); and Wagner et al., Proc. Natl. Acad. Sci. U.S.A. 87:3410-3414 (1990), both incorporated by reference. For review of gene marking and gene therapy protocols see Anderson et al., Science 256:808-813 (1992), incorporated by reference.

In a preferred embodiment, variant TNF-α genes are administered as DNA vaccines, either single genes or combinations of variant TNF-α genes. Naked DNA vaccines are generally known in the art. Brower, Nature Biotechnology, 16:1304-1305 (1998). Methods for the use of genes as DNA vaccines are well known to one of ordinary skill in the art, and include placing a variant TNF-α gene or portion of a variant TNF-α gene under the control of a promoter for expression in a patient in need of treatment. The variant TNF-α gene used for DNA vaccines can encode full-length variant TNF-α proteins, but more preferably encodes portions of the variant TNF-α proteins including peptides derived from the variant TNF-α protein. In a preferred embodiment, a patient is immunized with a DNA vaccine comprising a plurality of nucleotide sequences derived from a variant TNF-α gene. Similarly, it is possible to immunize a patient with a plurality of variant TNF-α genes or portions thereof as defined herein. Without being bound by theory, expression of the polypeptide encoded by the DNA vaccine, cytotoxic T-cells, helper T-cells and antibodies are induced, which recognize and destroy or eliminate cells expressing TNF-α proteins.

In a preferred embodiment, the DNA vaccines include a gene encoding an adjuvant molecule with the DNA vaccine.

Such adjuvant molecules include cytokines that increase the immunogenic response to the variant TNF-α polypeptide encoded by the DNA vaccine. Additional or alternative adjuvants are known to those of ordinary skill in the art and find use in the invention.

Pharmaceutical compositions are contemplated wherein a TNF-α variant of the present invention and one or more therapeutically active agents are formulated. Formulations of the present invention are prepared for storage by mixing TNF-α variant having the desired degree of purity with optional pharmaceutically acceptable carriers, excipients or stabilizers (Remington's Pharmaceutical Sciences 16th edition, Osol, A. Ed., 1980, incorporated entirely by reference), in the form of lyophilized formulations or aqueous solutions. Lyophilization is well known in the art, see, e.g., U.S. Pat. No. 5,215,743, incorporated entirely by reference. Acceptable carriers, excipients, or stabilizers are nontoxic to recipients at the dosages and concentrations employed, and include buffers such as histidine, phosphate, citrate, acetate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl orbenzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; sweeteners and other flavoring agents; fillers such as microcrystalline cellulose, lactose, corn and other starches; binding agents; additives; coloring agents; salt-forming counter-ions such as sodium; metal complexes (e.g. Zn-protein complexes); and/or non-ionic surfactants such as TWEEN®, PLURONICS® or polyethylene glycol (PEG). In a preferred embodiment, the pharmaceutical composition that comprises the TNF-α variant of the present invention may be in a water-soluble form. The TNF-α variant may be present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine. The formulations to be used for in vivo administration are preferably sterile. This is readily accomplished by filtration through sterile filtration membranes or other methods.

Controlled Release

In addition, any of a number of delivery systems are known in the art and may be used to administer TNF-α variants in accordance with embodiments of the present invention. Examples include, but are not limited to, encapsulation in liposomes, microparticles, microspheres (e.g. PLA/PGA microspheres), and the like. Alternatively, an implant of a porous, non-porous, or gelatinous material, including membranes or fibers, may be used. Sustained release systems may comprise a polymeric material or matrix such as polyesters, hydrogels, poly(vinylalcohol), polylactides, copolymers of L-glutamic acid and ethyl-L-gutamate, ethylene-vinyl acetate, lactic acid-glycolic acid copolymers such as the LUPRON DEPOT®, and poly-D-(−)-3-hydroxyburyric acid. It is also possible to administer a nucleic acid encoding the TNF-α of the current invention, for example by retroviral infection, direct injection, or coating with lipids, cell surface receptors, or other transfection agents. In all cases, controlled release systems may be used to release the TNF-α at or close to the desired location of action.

The pharmaceutical compositions may also include one or more of the following: carrier proteins such as serum albumin; buffers such as NaOAc; fillers such as microcrystalline cellulose, lactose, corn and other starches; binding agents; sweeteners and other flavoring agents; coloring agents; and polyethylene glycol. Additives are well known in the art, and are used in a variety of formulations. In a further embodiment, the variant TNF-α proteins are added in a micellular formulation; see U.S. Pat. No. 5,833,948, incorporated entirely by reference. Alternatively, liposomes may be employed with the TNF-α proteins to effectively deliver the protein. Combinations of pharmaceutical compositions may be administered. Moreover, the TNF-α compositions of the present invention may be administered in combination with other therapeutics, either substantially simultaneously or co-administered, or serially, as the need may be. The pharmaceutical compositions may also include one or more of the following: carrier proteins such as serum albumin; buffers such as NaOAc; fillers such as microcrystalline cellulose, lactose, corn and other starches; binding agents; sweeteners and other flavoring agents; coloring agents; and polyethylene glycol. Additives are well known in the art, and are used in a variety of formulations. In a further embodiment, the variant TNF-α proteins are added in a micellular formulation; see U.S. Pat. No. 5,833,948, incorporated entirely by reference. Alternatively, liposomes may be employed with the TNF-α proteins to effectively deliver the protein. Combinations of pharmaceutical compositions may be administered. Moreover, the TNF-α compositions of the present invention may be administered in combination with other therapeutics, either substantially simultaneously or co-administered, or serially, as the need may be.

Dosage forms for the topical or transdermal administration of a DN-TNF-protein disclosed herein include powders, sprays, ointments, pastes, creams, lotions, gels, solutions, patches and inhalants. The DN-TNF-protein may be mixed under sterile conditions with a pharmaceutically-acceptable carrier, and with any preservatives, buffers, or propellants which may be required. Powders and sprays can contain, in addition to the DN-TNF-protein, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Methods of Administration

The administration of the selective inhibitor of solTNF in accordance with embodiments of the present invention, preferably in the form of a sterile aqueous solution, is done peripherally, in a variety of ways, including, but not limited to, orally, subcutaneously, intravenously, intranasally, transdermally, intraperitoneally, intramuscularly, intrapulmonary, vaginally, rectally, or intraocularly. In some instances, the selective inhibitor of solTNF may be directly applied as a solution, salve, cream or spray. The selective inhibitor of solTNF may also be delivered by bacterial or fungal expression into the human system (e.g., WO 04046346 A2, hereby incorporated by reference).

Subcutaneous

Subcutaneous administration may be preferable in some circumstances because the patient may self-administer the pharmaceutical composition. Many protein therapeutics are not sufficiently potent to allow for formulation of a therapeutically effective dose in the maximum acceptable volume for subcutaneous administration. This problem may be addressed in part by the use of protein formulations comprising arginine-HCl, histidine, and polysorbate. A selective inhibitor of solTNF may be more amenable to subcutaneous administration due to, for example, increased potency, improved serum half-life, or enhanced solubility.

Intravenous

As is known in the art, protein therapeutics are often delivered by IV infusion or bolus. The selective inhibitor of solTNF may also be delivered using such methods. For example, administration may be by intravenous infusion with 0.9% sodium chloride as an infusion vehicle.

Inhaled

Pulmonary delivery may be accomplished using an inhaler or nebulizer and a formulation comprising an aerosolizing agent. For example, inhalable technology, or a pulmonary delivery system may be used. The selective inhibitor of solTNF may be more amenable to intrapulmonary delivery. The selective inhibitor of solTNF may also be more amenable to intrapulmonary administration due to, for example, improved solubility or altered isoelectric point.

Oral Delivery

Furthermore, the selective inhibitor of solTNF may be more amenable to oral delivery due to, for example, improved stability at gastric pH and increased resistance to proteolysis.

Transdermal

Transdermal patches may have the added advantage of providing controlled delivery of the selective inhibitor of solTNF to the body. Dissolving or dispersing DN-TNF-protein in the proper medium can make such dosage forms. Absorption enhancers can also be used to increase the flux of DN-TNF-protein across the skin. Either providing a rate controlling membrane or dispersing DN-TNF-protein in a polymer matrix or gel can control the rate of such flux.

Intraocular

Ophthalmic formulations, eye ointments, powders, solutions and the like, are also contemplated as being suitable for use in embodiments of this invention.

In a preferred embodiment, the selective inhibitor of solTNF is administered as a therapeutic agent, and can be formulated as outlined above. Similarly, variant TNF-α genes (including both the full-length sequence, partial sequences, or regulatory sequences of the variant TNF-α coding regions) may be administered in gene therapy applications, as is known in the art. These variant TNF-α genes can include antisense applications, either as gene therapy (i.e. for incorporation into the genome) or as antisense compositions, as will be appreciated by those in the art.

In a preferred embodiment, the nucleic acid encoding the variant TNF-α proteins may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., Proc. Natl. Acad. Sci. U.S.A. 83:4143-4146 (1986), incorporated entirely by reference). The oligonucleotides can be modified to enhance their uptake, e.g. by substituting their negatively charged phosphodiester groups by uncharged groups.

Dosage

Dosage may be determined depending on the complication being treated and mechanism of delivery. Typically, an effective amount of the selective inhibitor of solTNF, sufficient for achieving a therapeutic or prophylactic effect, range from about 0.000001 mg per kilogram body weight per day to about 10,000 mg per kilogram body weight per day. Suitably, the dosage ranges are from about 0.0001 mg per kilogram body weight per day to about 2000 mg per kilogram body weight per day. An exemplary treatment regime entails administration once every day or once a week or once a month. A DN-TNF protein may be administered on multiple occasions. Intervals between single dosages can be daily, weekly, monthly or yearly. Alternatively, A DN-TNF protein may be administered as a sustained release formulation, in which case less frequent administration is required. Dosage and frequency vary depending on the half-life of the agent in the subject. The dosage and frequency of administration can vary depending on whether the treatment is prophylactic or therapeutic. In prophylactic applications, a relatively low dosage is administered at relatively infrequent intervals over a long period of time. Some subjects continue to receive treatment for the rest of their lives. In therapeutic applications, a relatively high dosage at relatively short intervals is sometimes required until progression of the disease is reduced or terminated, and preferably until the subject shows partial or complete amelioration of symptoms of disease. Thereafter, the patent can be administered a prophylactic regime.

Toxicity

Suitably, an effective amount (e.g., dose) of a DN-TNF protein described herein will provide therapeutic benefit without causing substantial toxicity to the subject. Toxicity of the agent described herein can be determined by standard pharmaceutical procedures in cell cultures or experimental animals, e.g., by determining the LD50 (the dose lethal to 50% of the population) or the LD100 (the dose lethal to 100% of the population). The dose ratio between toxic and therapeutic effect is the therapeutic index. The data obtained from these cell culture assays and animal studies can be used in formulating a dosage range that is not toxic for use in human. The dosage of the agent described herein lies suitably within a range of circulating concentrations that include the effective dose with little or no toxicity. The dosage can vary within this range depending upon the dosage form employed and the route of administration utilized. The exact formulation, route of administration and dosage can be chosen by the individual physician in view of the subject's condition. See, e.g., Fingl et al., In: The Pharmacological Basis of Therapeutics, Ch. 1 (1975).

Conclusion

A method is disclosed for treating complications related to acute or chronic hyperglycemia, the method comprises: determining a level of lipocalin-2 (LCN2) in a patient; and if the level of LCN2 is greater than a predetermined-value, administering to the patient a therapeutically effective amount of a selective inhibitor of soluble tumor necrosis factor (solTNF), whereby said complications are treated.

In some embodiments, the selective inhibitor of solTNF comprises: a dominant negative tumor necrosis factor (DN-TNF)-α protein, a nucleic acid encoding the DN-TNF-α protein, or a combination thereof. In a preferred embodiment, the DN-TNF-α protein is XPRO1595.

In certain embodiments, the level of LCN2 comprises a urine-derived LCN2 level, and the predetermined value comprises 20 ng/mL LCN2.

In other embodiments, the level of LCN2 comprises a serum-derived LCN2 level, and the predetermined value comprises 140 ng/mL LCN2.

In other embodiments, the level of LCN2 comprises a plasma-derived LCN2 level, and the predetermined value comprises 110 ng/mL LCN2.

In still other embodiments, the level of LCN2 comprises a saliva-derived LCN2 level, and the predetermined value comprises 500 ng/mL.

In various embodiments, the complications of acute or chronic hyperglycemia or diet-induced obesity comprise diabetes mellitus; insulin resistance; hepatic steatosis; non-alcoholic hepatic steatosis; fibrotic liver disease, and vascular disease.

In an embodiment, the method comprises administering XPRO1595 in a dose between 0.1 mg/kg and 10.0 mg/kg.

In an embodiment, the selective inhibitor of solTNF is administered intravenously; subcutaneously; orally; via aerosol; via topical application; or via gene therapy.

In one embodiment, the DN-TNF-α protein is administered via gene modified autologous or allogeneic cellular therapy. The gene therapy may implement mesenchymal stem cells expressing a construct of the DN-TNF-α protein.

In some embodiments, the method further includes: measuring one or more markers of inflammation to confirm therapeutic potential of the selective inhibitor of solTNF, wherein each of the one or more markers of inflammation is selected from the group consisting of: C-reactive protein (CRP), interleukin 6 (IL-6); tumor necrosis alpha (TNF-alpha); lipocalin 2 (LCN-2); myeloid-derived suppressor cells (MDSCs); Eotaxin, Eotaxin-3, Flt-1NEGFR-1, ICAM-1, IFN-γ, IL-1α, IL-1β, IL-10, IL-12/IL-23p40, IL-13, IL-15, IL-16, IL-17A, IL-2, IL-4, IL-5, IL-7, IL-8, IP-10, MCP-1, MCP-4, MCP-5, MDC, MIP-1α, MIP-1β, PlGF, SAA, TARC, Tie-2, VCAM-1, VEGF-A, VEGF-C, VEGF-D, FGF, fractalkine, 6Ckine/Exodus-2/SLC/MIP-3, GCP-2, TECK, IP-10, CINC 2, and prostaglandins. More preferably, the markers of inflammation are each selected from the group consisting of: c-reactive protein (CRP), interleukin 6 (IL-6), tumor necrosis alpha (TNF-alpha), lipocalin 2 (LCN-2), IFN-γ, IL-1a, IL-1β, IL-10, IL-17A, Vascular Endothelial Growth Factor (VEGF), Epidermal Growth Factor (EGF), Interferon-γ (IFN-γ), Monocyte Chemotactic Protein-1 (MCP-1), and prostaglandins.

In some embodiments, the method includes administering the DN-TNF-α protein only if the one or more markers of inflammation confirm metabolic inflammation in the patient.

In another embodiment, a method for treating insulin resistance in a patient comprises: determining fasting insulin level in the patient; and if the fasting insulin level is greater than 25 mIU/L or 174 pmol/L, administering to the patient a therapeutically effective dose of a selective inhibitor of soluble tumor necrosis factor (solTNF), whereby said insulin resistance is treated.

In an embodiment, the method comprises determining homeostasis model assessment (HOMA) in the patient for assessing insulin resistance, and if the patient is determined to suffer from insulin resistance, administering to the patient a therapeutically effective dose of a selective inhibitor of solTNF.

In an embodiment, the method comprises determining insulin-to-glucose ratio in the patient for assessing insulin resistance, and if the patient is determined to suffer from insulin resistance, administering to the patient a therapeutically effective dose of a selective inhibitor of solTNF.

In an embodiment, the method comprises determining Bennet index in the patient for assessing insulin resistance, and if the patient is determined to suffer from insulin resistance, administering to the patient a therapeutically effective dose of a selective inhibitor of solTNF.

In yet another embodiment, a method for treating fatty liver disease in a patient comprises: confirming that a patient suffers from fatty liver disease; and administering a therapeutically effective dose of a selective inhibitor of soluble tumor necrosis factor (solTNF) to the patient, whereby said fatty liver disease is treated. In a preferred embodiment, the selective inhibitor of solTNF is XPRO1595.

EXAMPLES

Example 1

Figure 3B:
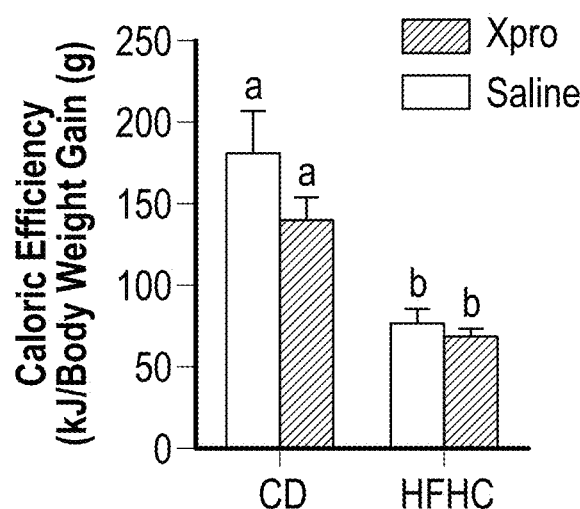
FIG. 3B shows caloric efficiency for each of a control diet group and an HFHC diet group as obtained from the DIO rodent model.
Figure 3C:
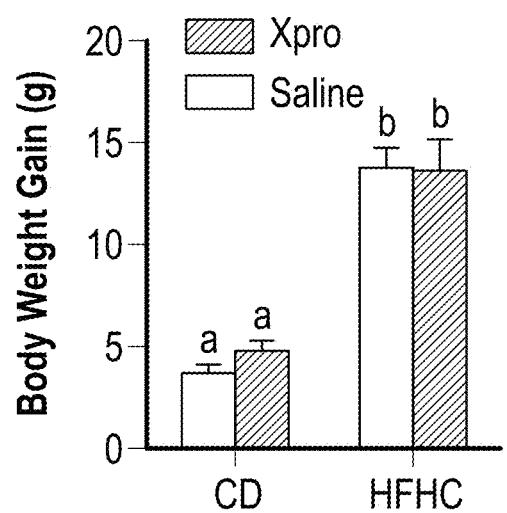
FIG. 3C shows body weight gain for each of a control diet group and an HFHC diet group as obtained from the DIO rodent model.
Figure 3D:
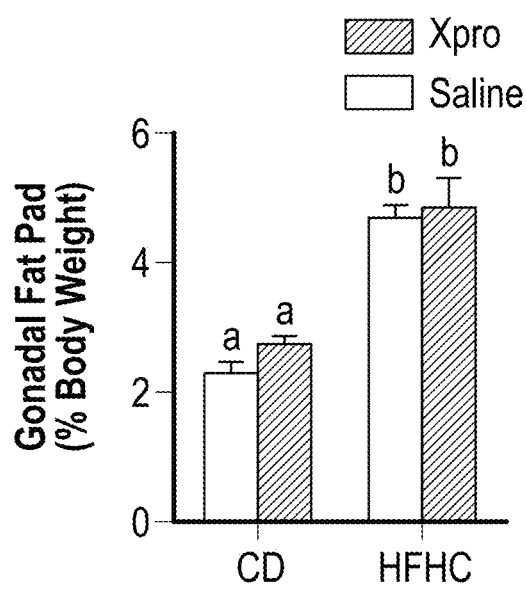
FIG. 3D shows gonadal fat pad for each of a control diet group and an HFHC diet group as obtained from the DIO rodent model.
Figure 3E:
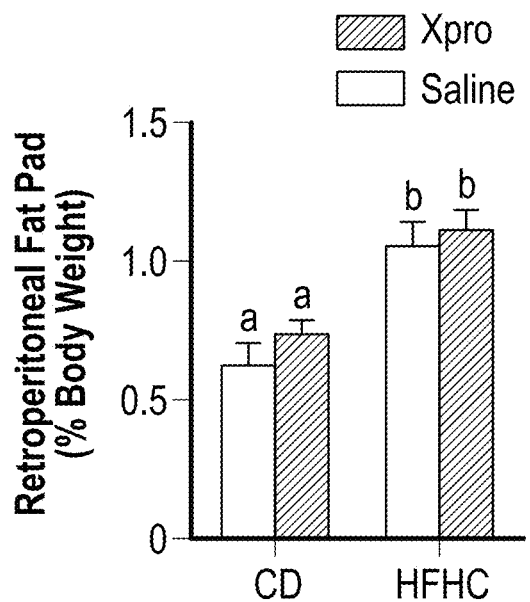
FIG. 3E retroperitoneal fat pad for each of a control diet group and an HFHC diet group as obtained from the DIO rodent model.
Figure 3F:
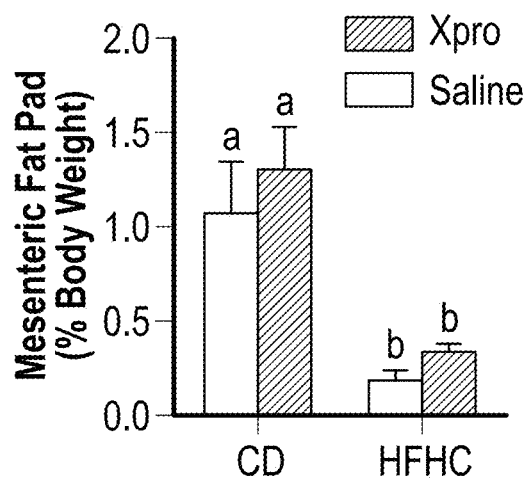
FIG. 3F shows mesenteric fat pad for each of a control diet group and an HFHC diet group as obtained from the DIO rodent model.

Soluble TNF Neutralization Decreases Insulin and LCN2 Plasma Levels in Diet-Induced Metabolic Inflammation A previously published diet-induced obesity (DIO) animal model was used with minor modifications to assess the peripheral and central effects of a high-fat high-carbohydrate (HFHC) diet and solTNF neutralization in obesity (Maria Elizabeth de Sousa Rodrigues et al., Brain Behav Immun. 2017 January; 59: 158-172). As expected, as shown in FIG. 3A, high-fat, high-carbohydrate (HFHC)-fed mice exhibited significant body-weight gain compared to control diet (CD) groups starting in the third week of diet treatment. Fourteen weeks of HFHC diet consumption was associated with reduced caloric efficiency (FIG. 3B) ($p<0.0001$), increased body-weight gain ($p<0.0001$) (FIG. 3C) and weight of retroperitoneal ($p<0.0001$) and gonadal fat pads ($p<0.0001$) (FIGS. 3D-E). HFHC diet decreased mesenteric tissue weight ($p<0.0001$) in both HFHC diet/Saline and HFHC diet/XPRO1595 groups (FIG. 3F).

HFHC diet consumption promoted metabolic dysregulation (Table 1, below) evidenced by increased plasma cholesterol ($p<0.0001$), leptin ($p<0.0001$), and insulin levels ($p=0.0005$). A HFHC diet and XPRO1595 interaction promoted a decrease in circulating insulin ($p=0.007$). A metabolic inflammatory profile in HFHC-fed mice was demonstrated (Table 1) by an increase in plasma levels of the acute phase protein LCN2 ($p<0.0001$) as well as classically proinflammatory cytokines IL-6 ($p=0.0001$) and TNF ($p=0.0072$) (FIG. 4B). solTNF neutralization with XPRO1595 decreased LCN2 levels in the HFHC diet group ($p=0.0397$) and reduced IL-6 in HFHC-fed mice to levels statistically indistinguishable from CD-fed mice. HFHC diet decreased plasma triglycerides in both HFHC-fed groups ($p=0.0057$) (Table 1).

TABLE 1

Soluble TNF neutralization decreases insulin and LCN2 plasma levels in diet-induced metabolic inflammation

|  | CD Saline | CD XPro | HFHC Saline | HFHC XPro |
|---|---|---|---|---|
| Insulin (ng/mL) | 0.91 ± 0.13 [a] | 1.89 ± 0.38 [a] | 6.97 ± 1.63 [b] | 2.76 ± 0.62 [b] |
| Leptin (ng/mL) | 4.80 ± 0.64 [a] | 6.90 ± 1.32 [a] | 84.46 ± 24.84 [b] | 67.45 ± 16.10 [b] |
| Cholesterol (mg/dL) | 88.88 ± 22.79 [a] | 79.00 ± 5.23 [a] | 234.80 ± 35.87 [b] | 183.81 ± 24.91 [b] |
| Triglycerides (mg/dL) | 38.53 ± 7.41 [ab] | 57.35 ± 6.70 [a] | 31.49 ± 4.65 [b] | 29.77 ± 2.77 [b] |
| IL-6 (pg/mL) | 1.80 ± 0.57 [a] | 1.94 ± 0.41 [a] | 7.82 ± 1.48 [b] | 5.22 ± 0.93 [ab] |
| LCN2 (ug/mL) | 56.01 ± 7.03 [ac] | 39.11 ± 2.53 [a] | 80.92 ± 6.75 [b] | 72.18 ± 6.36 [bc] |

*Different letters indicate significant differences in mean values.
Data analyzed by two-way ANOVA followed by Tukey's multiple comparisons test in GraphPad Prism 6.
n = 10-15/group.
CD, Control diet;
HFHC, High-fat high-carbohydrate;
IL-6, interleukin-6;
LCN2, Lipocalin-2.

Example 2

Figure 3G:
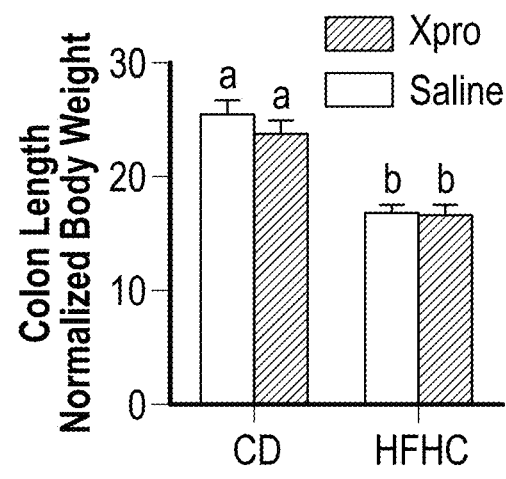
FIG. 3G shows colon length normalized by body weight for each of a control diet group and an HFHC diet group as obtained from the DIO rodent model.
Figure 3H:
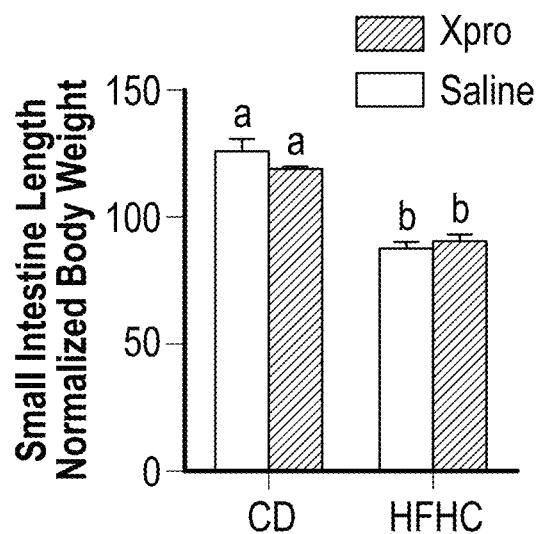
FIG. 3H shows small intestine length normalized by body weight for each of a control diet group and an HFHC diet group as obtained from the DIO rodent model.
Figure 5A:
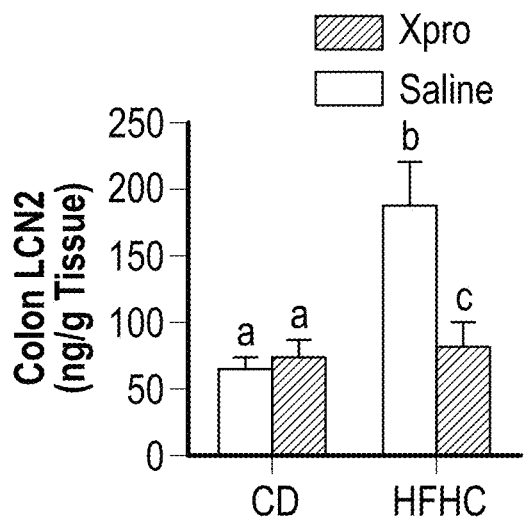
FIG. 5A shows colon LCN2 for each of a control diet group and an HFHC diet group as obtained from the DIO rodent model.
Figure 5B:
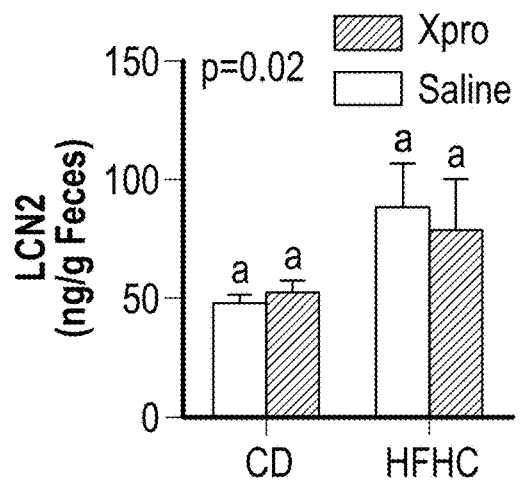
FIG. 5B shows fecal LCN2 for each of a control diet group and an HFHC diet group as obtained from the DIO rodent model.
Figure 5C:
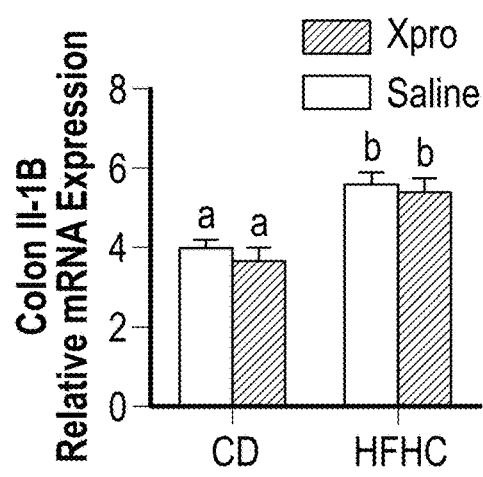
FIG. 5C shows colon Il-1B relative mRNA Expression for each of a control diet group and an HFHC diet group as obtained from the DIO rodent model.
Figure 6A:
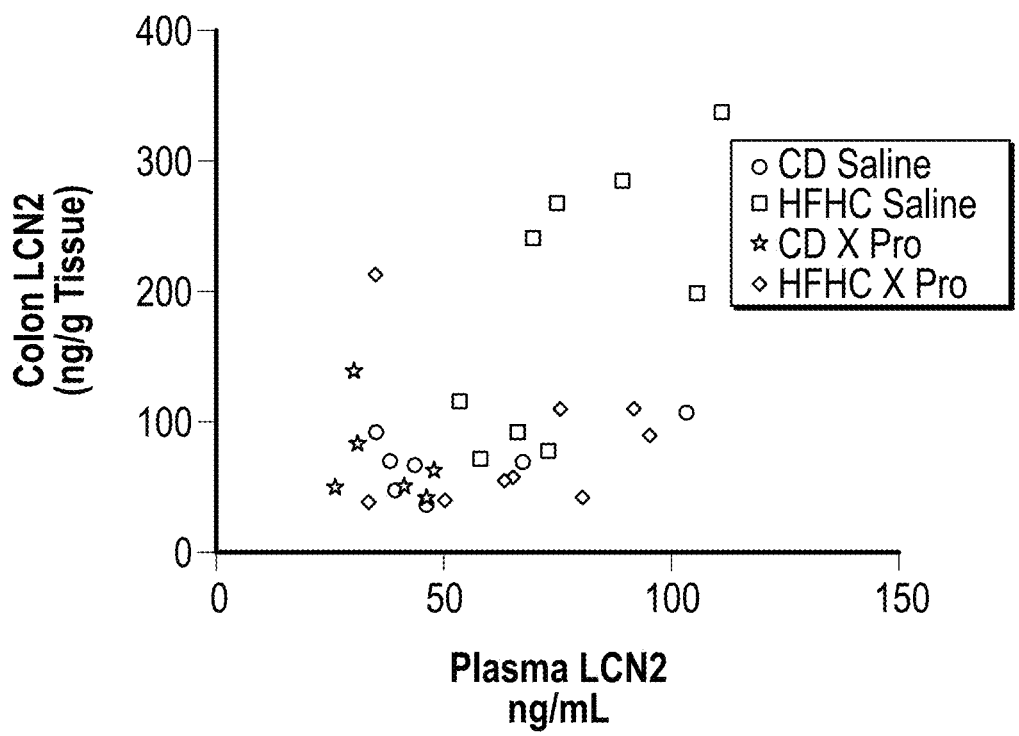
FIG. 6A shows scatter plot Pearson correlation between plasma and colonic LCN2 for each of control diet saline, control diet XPro, HFHC saline, and HFHC XPro groups as obtained from the DIO rodent model.
Figure 6B:
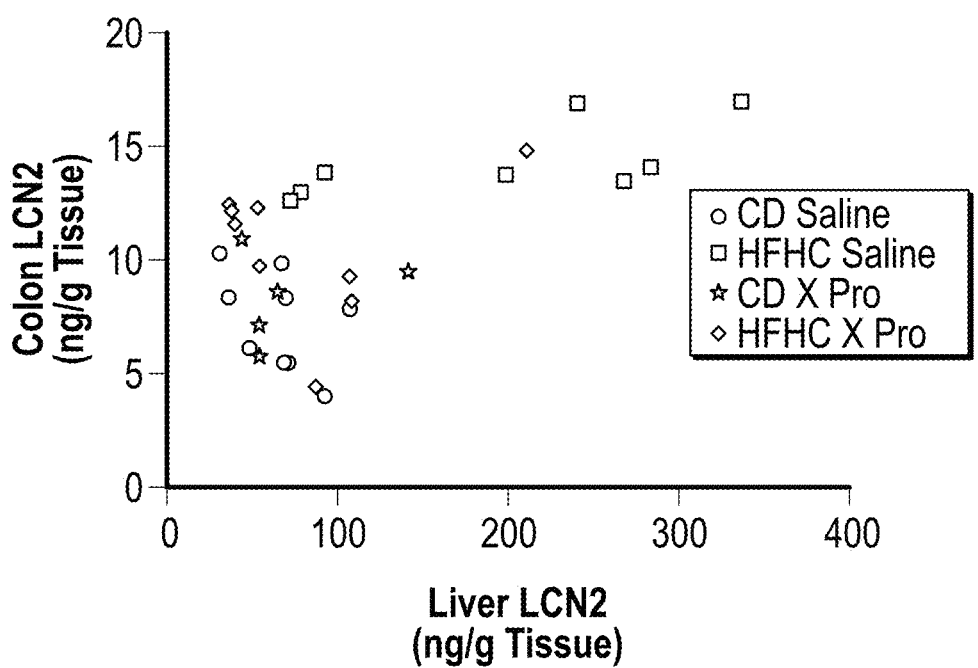
FIG. 6B shows scatter plots Pearson correlation between colonic and hepatic LCN2 for each of control diet saline, control diet XPro, HFHC saline, and HFHC XPro groups as obtained from the DIO rodent model.

SolTNF Inhibition Decreases Colonic LCN2 and Tight Junction Protein Alterations Associated with HFHC Diet Having observed differences in colon (p<0.0001) and small intestine lengths (p<0.0001) associated with HFHC diet consumption (FIG. 3G-H), the potential of DIO to promote alterations in the intestinal environment and the ability of solTNF neutralization to reverse those changes was investigated. Animals exposed to HFHC diet developed an inflammatory colonic profile demonstrated by elevated colonic (p=0.0091) and fecal (p=0.0252) LCN2 and IL-1β mRNA expression (p<0.0001) (FIGS. 5A-C). There was a detectable XPRO1595 effect (p=0.0460) of decreasing colonic LCN2 in HFHC diet but not in the CD group (FIG. 5A). Strong positive correlations between colonic LCN2 and plasma LCN2 (r=0.51, p=0.003), and colonic LCN2 and liver LCN2 (r=0.6603, p=0.0005), and plasma LCN2 were observed. (FIG. 6A-B).

Figure 5D:
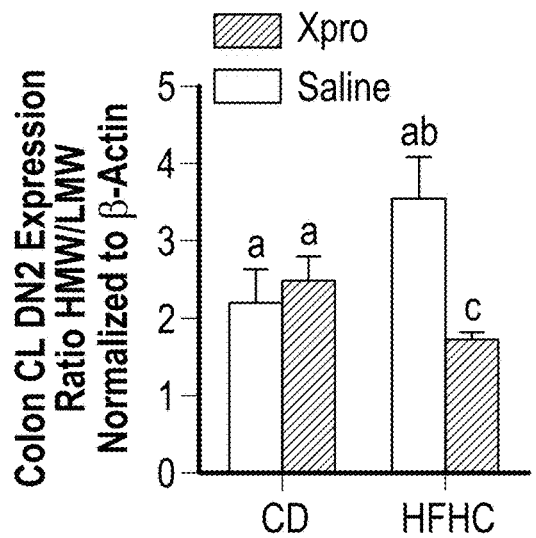
FIG. 5D shows colon CLDN2 mRNA expression ratio HMW/LMW normalized to β-actin for each of a control diet group and an HFHC diet group as obtained from the DIO rodent model.
Figure 5E:
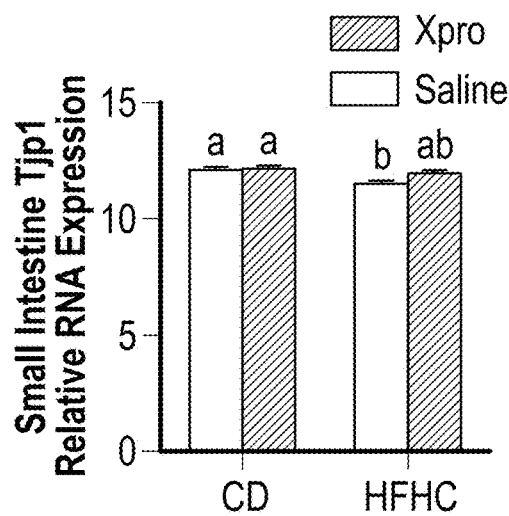
FIG. 5E shows small intestine Tjpl relative RNA expression for each of a control diet group and an HFHC diet group as obtained from the DIO rodent model.
Figure 5F:
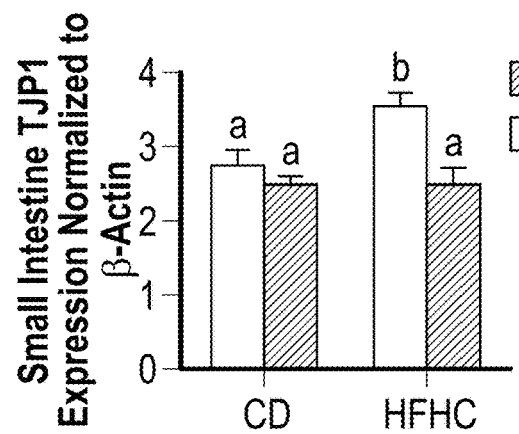
FIG. 5F shows small intestine TJP1 protein expression normalized to β-actin for each of a control diet group and an HFHC diet group as obtained from the DIO rodent model.

In addition to these inflammatory changes, the HFHC diet and XPRO1595 interaction impacted the high/low ratio of the permeability-promoting Claudin-2 protein in the colon (p=0.0091). solTNF inhibition decreased the ratio of Claudin-2 high/low in the HFHC diet/XPRO1595 group (p=0.0425) (FIG. 5D). HFHC diet/Saline mice exhibited decreased tight junction protein 1 (Tjpl, Zo-1) mRNA expression (p=0.0007) and an increase in ZO-1 protein levels (p=0.05) in the small intestine compared to CD groups (FIG. 5E-F). XPRO1595 treatment attenuated the increase in Tjpl protein (p=0.0027) in the small intestine (p=0.0027) (FIG. 5F). No significant changes were observed in Occludin mRNA or protein levels in the colon or small intestine between the experimental groups.

Example 3

Figure 4A:
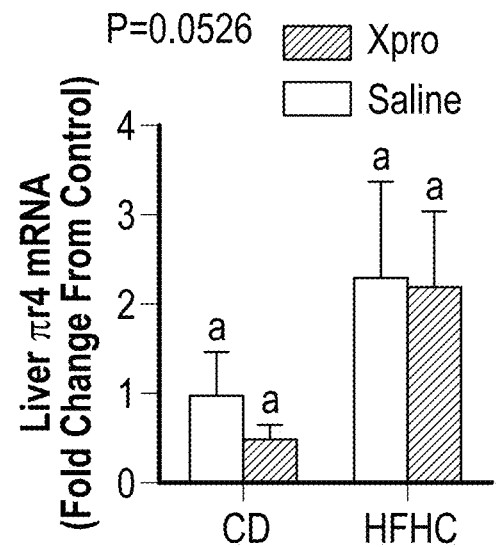
FIG. 4A shows liver Tlr4 mRNA for each of a control diet group and an HFHC diet group as obtained from the DIO rodent model.
Figure 4B:
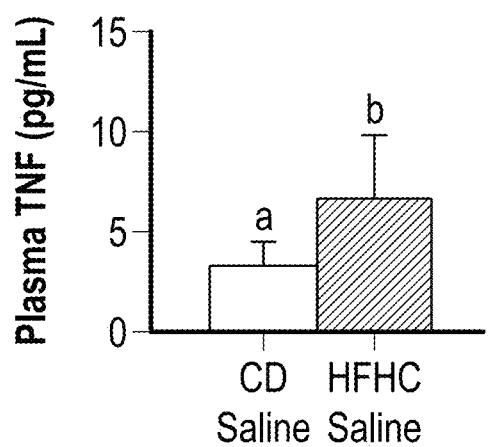
FIG. 4B shows plasma TNF for each of a control diet group and an HFHC diet group as obtained from the DIO rodent model.
Figure 7A:
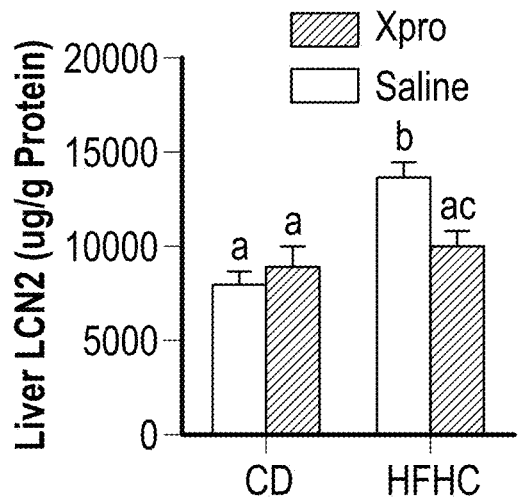
FIG. 7A shows liver LCN2 for each of a control diet group and an HFHC diet group as obtained from the DIO rodent model.
Figure 7B:
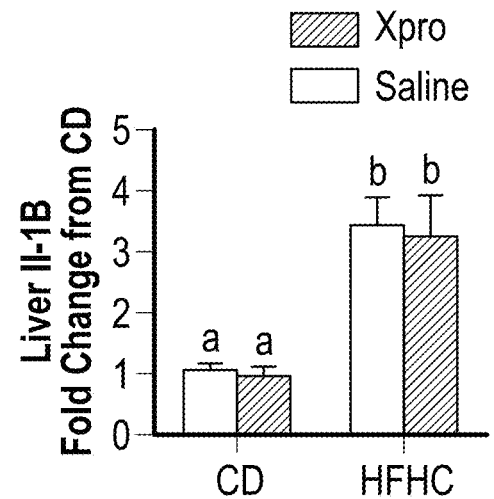
FIG. 7B shows liver HFHC Il-1B mRNA fold change from a control diet group as obtained from the DIO rodent model.
Figure 7C:
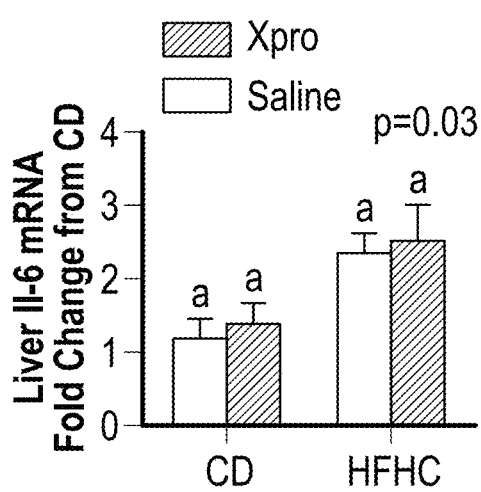
FIG. 7C shows liver HFHC Il-6 mRNA fold change from a control diet group as obtained from the DIO rodent model.
Figure 7D:
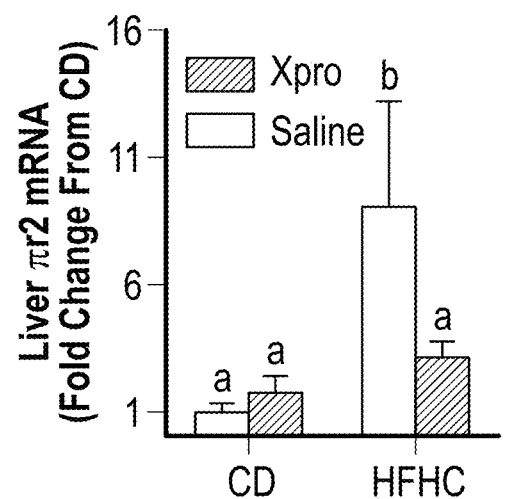
FIG. 7D shows liver HFHC Tlr2 mRNA fold change from a control diet group as obtained from the DIO rodent model.
Figure 7E:
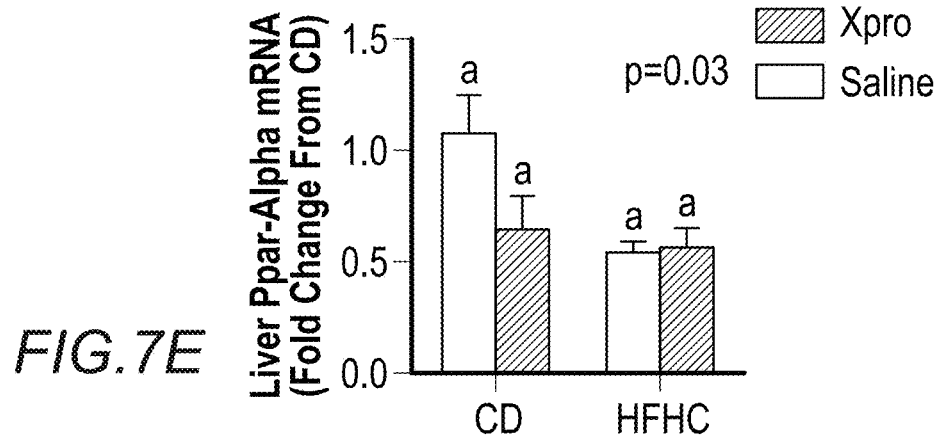
FIG. 7E shows liver HFHC Ppar-alpha mRNA fold change from a control diet group as obtained from the DIO rodent model.

SolTNF Inhibition Reduces Hepatic LCN2 Levels in the Presence of Diet-Induced Liver Inflammation To gain further insight into the resultant immune alterations present in the gut-liver axis, hepatic LCN2 levels and the expression of inflammatory factors in the liver tissue were assessed. HFHC diet-fed mice developed elevated concentrations of hepatic LCN2 (p=0.034), and a significant interaction between diet and XPRO1595 treatment was found (p=0.0034), with LCN2 levels in the HFHC diet/XPRO1595 group indistinguishable from the CD group (FIG. 7A). The hepatic inflammatory profile after 14 weeks of HFHC diet treatment was confirmed by an increase in hepatic Il-1b (p<0.0001) and Il-6 (p=0.0036) mRNA expression (FIG. 7B-C). Diet treatment raised Tlr2 (p=0.022) and decreased Ppara (p=0.034) mRNA expression compared to CD groups (FIG. 7D-E). XPRO1595 decreased Tlr2 expression in HFHC diet-treated mice to levels statistically indistinguishable from the CD group. XPRO1595 reduced Ppara levels in the CD group. There was no significant difference in hepatic Tlr4 or Tlr9 between the experimental groups (FIG. 4A-B).

Example 4

HFHC Diet Impacts Hepatic Insulin Signaling and Promotes Hepatic Steatosis

Figure 8:
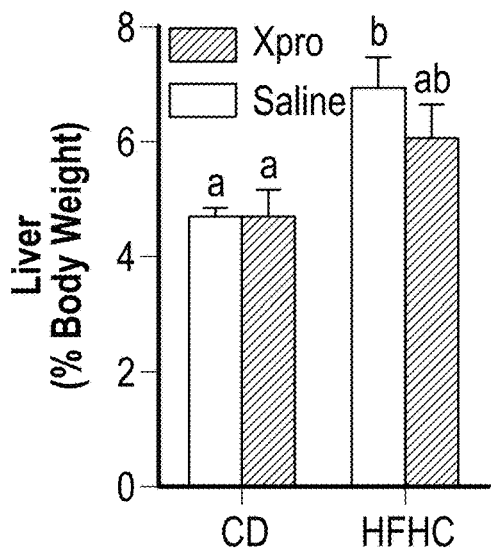
FIG. 8 shows liver percent body weight for each of a control diet group and an HFHC diet group as obtained from the DIO rodent model.
Figure 9A:
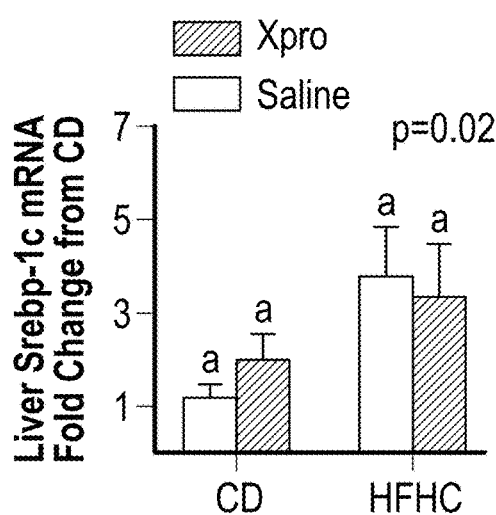
FIG. 9A shows liver HFHC Srebp-1c mRNA fold change from a control diet group as obtained from the DIO rodent model.
Figure 9B:
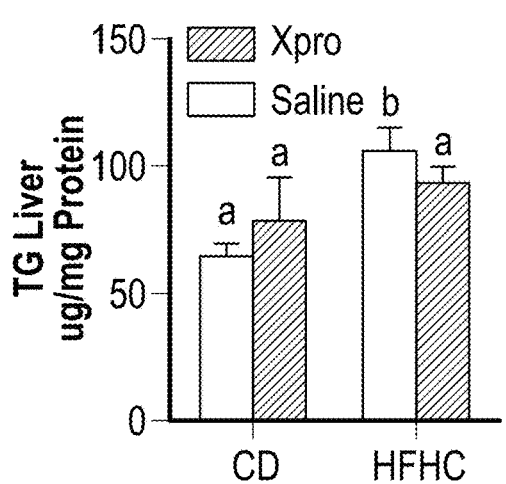
FIG. 9B shows TG liver protein for each of a control diet group and an HFHC diet group as obtained from the DIO rodent model.
Figure 9C:
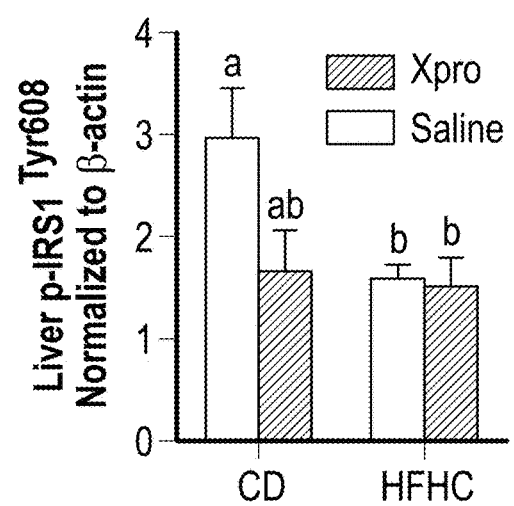
FIG. 9C shows liver p-IRS1 TYR 608 normalized to β-actin for each of a control diet group and an HFHC diet group as obtained from the DIO rodent model.
Figure 9D:
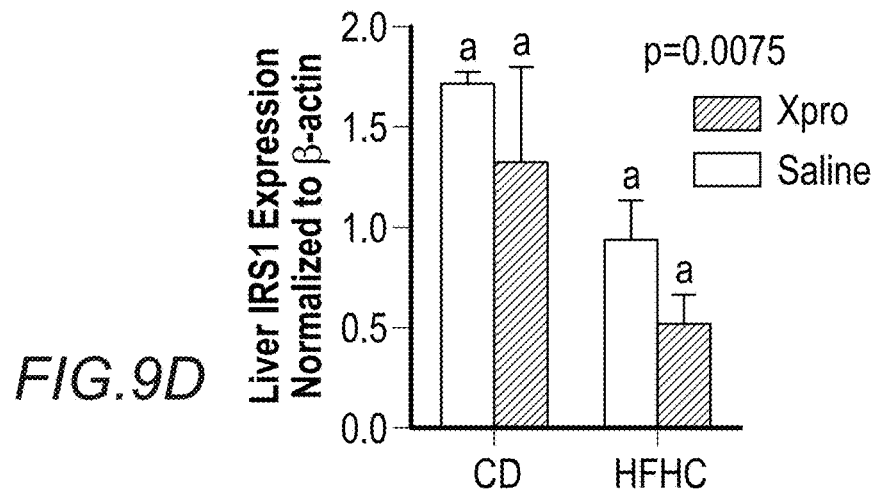
FIG. 9D shows liver IRS1 expression normalized to β-actin for each of a control diet group and an HFHC diet group as obtained from the DIO rodent model.

Differences in macroscopic gross liver appearance (histological sections of representative livers stained for Oil Red 0) and liver weight (FIG. 8) (p=0.0006) suggested hepatic lipid accumulation associated with HFHC consumption. Specifically, the Oil Red 0 staining of liver tissue sections revealed intense lipid deposition in the HFHC groups. This lipid deposition was partially corrected by XPRO1595 treatment. The disturbance in lipid metabolism was confirmed by the impact of the HFHC diet on sterol regulatory element-binding protein-1c (Srebp-1 c) mRNA expression (p=0.0263), a well-known transcription factor that controls lipids biosynthesis (FIG. 9A). Additionally, increased hepatic triglyceride accumulation (p=0.0102) was observed in the HFHC diet/Saline group compared to the CD group (p<0.0006) (FIG. 9B). The assessment of insulin signaling in isolated liver tissue revealed decreased IRS1 phosphorylation at tyrosine 608 (TYR 608) in the HFHF diet/Saline compared to the CD group (p=0.0372). A diet effect decreased the expression of IRS1 (p=0.0075) in the liver (FIG. 9C-D).

Example 5

HFHC Diet and solTNF Neutralization Leads to Differential Expression of Metabolic Features in Plasma and Liver Untargeted plasma and liver metabolomics were used to investigate the effect of HFHC diet on metabolic profiles and the extent to which solTNF neutralization reversed any alterations. HFHC diet promoted significant changes to the metabolic profile: 147 significant features below FDR≤0.05 were identified, including alterations in fatty acids and lipid intermediate metabolites. Mouse pathway enrichment using Mummichog analysis identified significant enrichment in nucleotides pathways, fuel utilization metabolism, urea cycle and mitochondrial bioenergetics (Table 2).

in purine, co-factors and inversions in pentose/glucuronate metabolisms suggest alterations in nucleotides pathways, hepatic metabolism and β-oxidation (Table 2).

An additional analysis was performed in order to identify differentially expressed features in the HFHC diet/Saline vs. HFHC diet/XPRO1595 mice to further understand XPRO1595 pharmacodynamics. Thirty-five features significant at p-value <0.05 decreased in HFHC diet/XPRO1595 relative to HFHC diet/Saline groups, suggesting additional pathway alterations occurring with solTNF-blocking treatment. Pathway changes occurring with solTNF blocking include a decrease in cholesterol products and tryptophan and inflammatory metabolites (FIG. 10A-C). XPRO1595 treatment showed no significant plasma metabolic alterations when administered to healthy control mice. Thus, no significant features at false discovery rate (FDR)≤0.2 were

TABLE 2

| Plasma metabolic pathways enriched by HFHC diet | | | | |
|---|---|---|---|---|
| Mouse metabolic pathways significantly enriched | Number of significant metabolites from HFHC diet | Total number of metabolites detected in pathway | Raw p value | Permutation corrected p value* |
| Purine ribonucleosides degradation to ribose-1-phosphate | 6 | 8 | 4.00E−05 | 0.0010 |
| Guanosine nucleotides degradation III | 4 | 7 | 0.0042 | 0.0012 |
| Urate biosynthesis/inosine 5'-phosphate degradation | 4 | 8 | 0.0077 | 0.0013 |
| Xanthine and xanthosine salvage | 3 | 6 | 0.0222 | 0.0020 |
| Adenine and adenosine salvage III | 3 | 7 | 0.0358 | 0.0024 |
| 3-phosphoinositide biosynthesis | 2 | 2 | 0.0129 | 0.0028 |
| Adenosine nucleotides degradation II | 3 | 8 | 0.0526 | 0.0029 |
| D-myo-inositol (1,4,5)-trisphosphate biosynthesis | 2 | 3 | 0.0359 | 0.0042 |
| Purine and pyrimidine metabolism | 4 | 19 | 0.1622 | 0.0057 |
| Xylitol degradation | 2 | 4 | 0.0666 | 0.0062 |
| Tyrosine degradation I | 2 | 5 | 0.1029 | 0.0088 |
| Coenzyme A biosynthesis | 2 | 5 | 0.1029 | 0.0088 |
| Adenine and adenosine salvage I | 2 | 5 | 0.1029 | 0.0088 |
| Glutamate degradation VII | 2 | 6 | 0.1432 | 0.0121 |
| Pyridoxal 5'-phosphate salvage pathway | 2 | 6 | 0.1432 | 0.0121 |
| Pyridine nucleotide cycling | 2 | 10 | 0.3210 | 0.0333 |
| Arginine biosynthesis IV | 2 | 10 | 0.3210 | 0.0333 |
| Salvage pathways of pyrimidine ribonucleotides | 2 | 11 | 0.3655 | 0.0407 |

*Mummichog derived p-values were determined by comparing metabolite-pathway distribution from randomly sampled m/z features to distribution for the diet-associated metabolites.

HFHC diet promoted plasma and hepatic metabolic changes in pathways frequently associated with insulin resistance and diabetic complications, such as alterations in purines, biopterin synthesis and D-myo-inositol (1,4,5)-trisphosphate biosynthesis. As a reference, the significant features from the HFHC diet metabolic profile were compared against a human metabolic model. Enriched pathways observed between CD/Saline and CD/XPRO1595 groups. Principal component analysis (PCA) of the liver samples revealed clustering discrimination among the experimental groups. The untargeted liver metabolomics identified 1098 polar and 2583 non-polar metabolic changes associated with HFHC diet consumption. These hepatic metabolic alterations included changes in purine, leukotrienes, butanoate and lipid metabolism. Co-factor molecules and intestinal bacterial products such as butyrate and glutamate pathways were altered with diet treatment (Table 3).

TABLE 3

Liver metabolic pathways significantly associated with HFHC diet-related metabolites.

| Mouse metabolic pathways significantly enriched | Number of significant metabolites from HFHC diet | Total number of metabolites detected in pathway | Raw p value | Permutation corrected p value* |
|---|---|---|---|---|
| Vitamin D3 (cholecalciferol) metabolism | 10 | 11 | 0.00116 | 0.0010 |
| Vitamin E metabolism | 19 | 30 | 0.01493 | 0.00109 |
| Purine metabolism | 27 | 51 | 0.07539 | 0.00182 |
| Leukotriene metabolism | 22 | 47 | 0.30474 | 0.01025 |
| Ascorbate (Vitamin C) and Aldarate metabolism | 12 | 24 | 0.28035 | 0.01144 |
| Biopterin metabolism | 8 | 15 | 0.26614 | 0.01338 |
| Linoleate metabolism | 10 | 20 | 0.31046 | 0.01558 |
| Glutamate metabolism | 7 | 13 | 0.28011 | 0.01629 |
| Sialic acid metabolism | 12 | 25 | 0.34453 | 0.1753 |
| Omega-3 fatty acid metabolism | 5 | 9 | 0.31271 | 0.2718 |
| Fatty acid metabolism | 7 | 14 | 0.36836 | 0.2878 |
| Glutathione metabolism | 6 | 12 | 0.39293 | 0.03761 |
| Vitamin B3 (Nicotinate and nicotinamide) metabolism | 9 | 20 | 0.48283 | 0.04795 |
| Pyruvate metabolism | 13 | 17 | 0.28612 | 0.03777 |
| Caffeine metabolism | 10 | 11 | 0.07635 | 0.01112 |
| Prostaglandin formation from dihomo gama-linoleic acid | 6 | 6 | 0.08897 | 0.1981 |
| Glycosphingolipid biosynthesis-ganglioseries | 8 | 9 | 0.14516 | 0.02261 |
| Butanoate metabolism | 16 | 21 | 0.25322 | 0.02804 |

*Mummichog derived p-values were determined by comparing metabolite-pathway distribution from randomly sampled m/z features to distribution for the diet-associated metabolites

Example 6

Figure 11A:
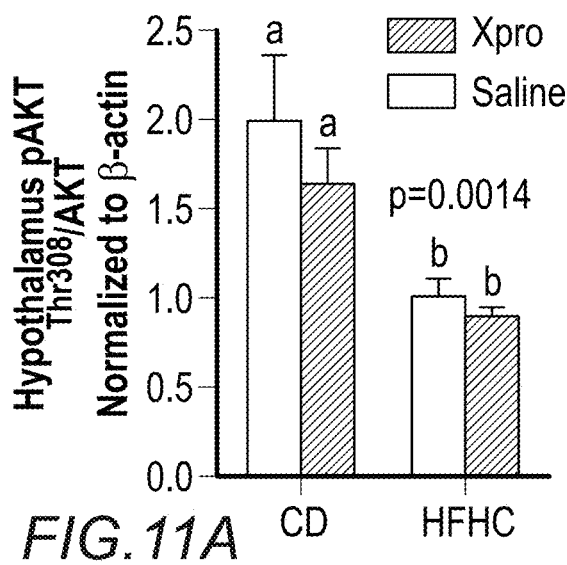
FIG. 11A shows hypothalamus pAKT Thr308/AKT expression normalized to β-actin for each of a control diet group and an HFHC diet group as obtained from the DIO rodent model.
Figure 11B:
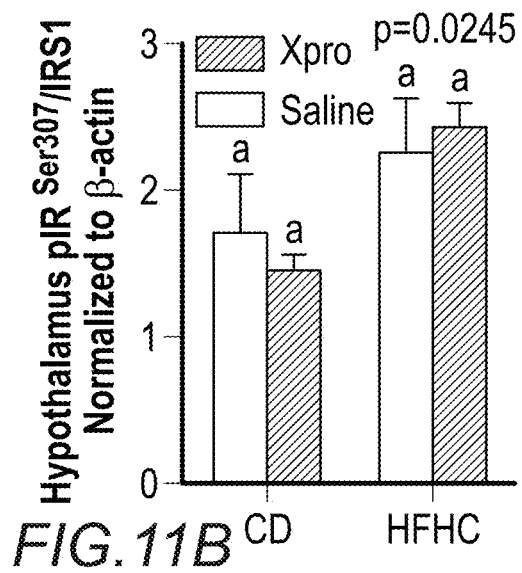
FIG. 11B shows hypothalamus pIR Ser307/IRS1 normalized to β-actin for each of a control diet group and an HFHC diet group as obtained from the DIO rodent model.
Figure 11C:
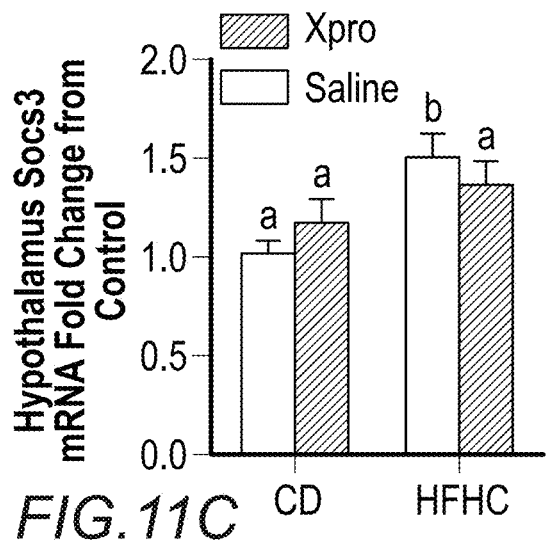
FIG. 11C shows hypothalamus HFHC Socs3 mRNA fold change from a control diet group as obtained from the DIO rodent model.
Figure 11D:
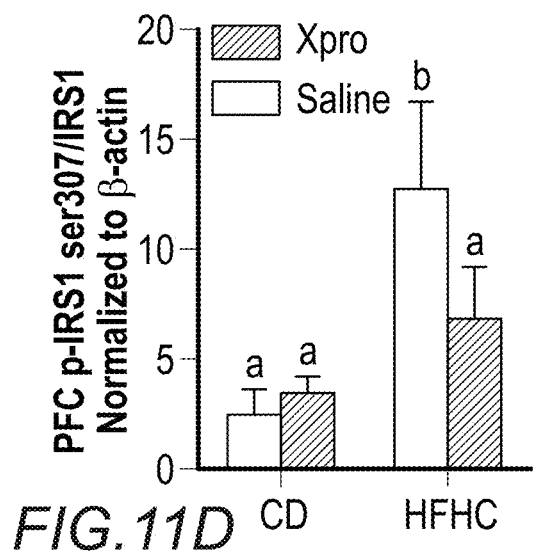
FIG. 11D shows prefrontal cortex p-IRS1 Ser307/IRS1 normalized to β-actin for each of a control diet group and an HFHC diet group as obtained from the DIO rodent model.
Figure 12A:
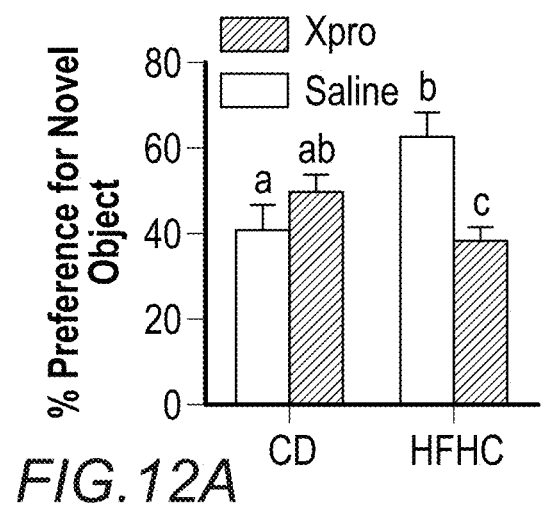
FIG. 12A shows percent preference for novel object for each of a control diet group and an HFHC diet group as obtained from the DIO rodent model.
Figure 12B:
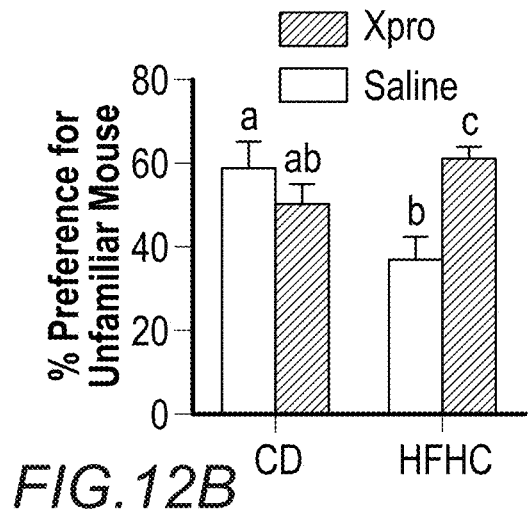
FIG. 12B shows percent preference for unfamiliar rodent for each of a control diet group and an HFHC diet group as obtained from the DIO rodent model.
Figure 12D:
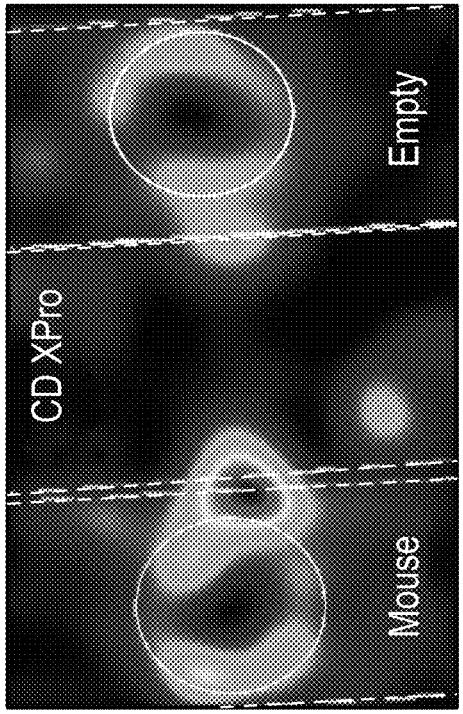
FIG. 12D shows a representative heat map demonstrating rodent activity described as time spent in each chamber of a three-chamber sociability test for a control diet-XPro test group.
Figure 12F:
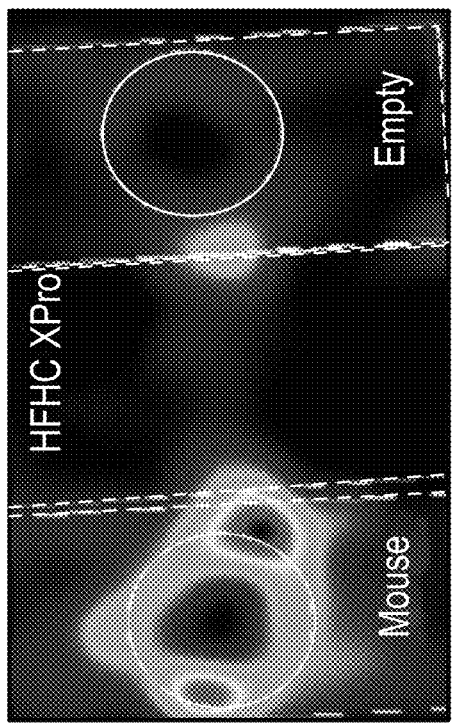
FIG. 12F shows a representative heat map demonstrating rodent activity described as time spent in each chamber of a three-chamber sociability test for a high-fat, high-carbohydrate diet-XPro group.
Figure 12C:
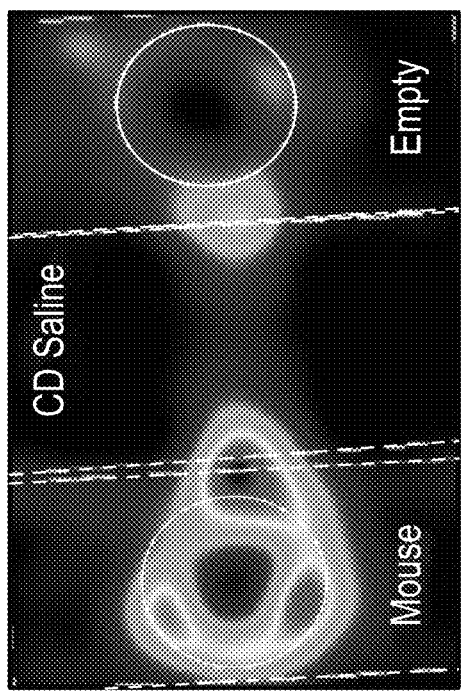
FIG. 12C shows a representative heat map demonstrating rodent activity described as time spent in each chamber of a three-chamber sociability test for a control diet-saline test group.
Figure 12E:
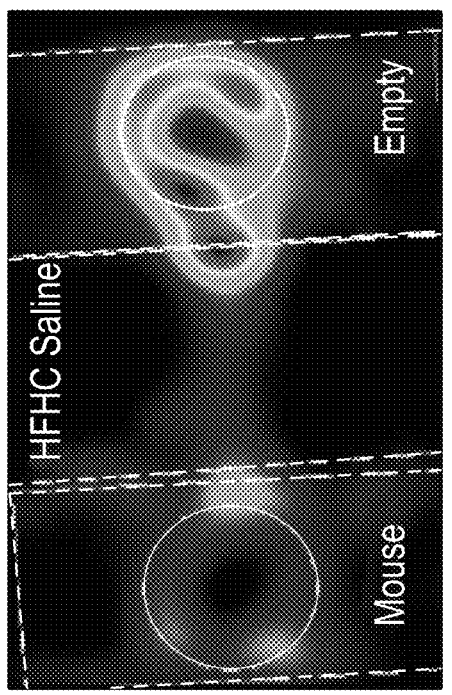
FIG. 12E shows representative heat map demonstrating rodent activity described as time spent in each chamber of a three-chamber sociability test for a high-fat, high-carbohydrate diet saline group.
Figure 13:
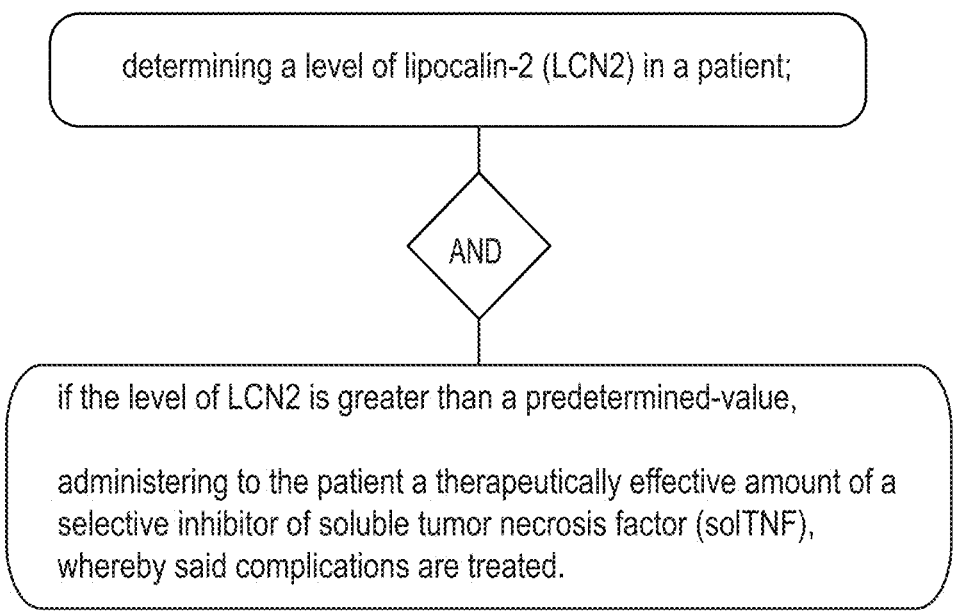
FIG. 13 shows a method for treating complications related to acute or chronic hyperglycemia.

HFHC Diet Impairs Insulin Signaling in the Hypothalamus and Pre-Frontal Cortex Because central insulin actions are associated with the regulation of hepatic and systemic energetic balance, the impact of DIO and solTNF inhibition on insulin signaling in the hypothalamus and the pre-frontal cortex (PFC) were assessed. There was a marked decrease in hypothalamic p-Akt Thr 308 phosphorylation in HFHC diet-fed groups compared to the CD/Saline group (p=0.0014) (FIG. 11A). HFHC diet increased Ser 307 phosphorylation of IRS in the hypothalamus (p=0.0245) (FIG. 11B) and Socs3 hypothalamic RNA expression (p=0.0018) (FIG. 11C). Increased phosphorylation of p-IRS1 Ser 307 in PFC (p=0.0117) was observed in the HFHC diet/Saline group (FIG. 11D). SolTNF neutralization with XPRO1595 reduced Ser 307 phosphorylation of IRS in PFC and Socs3 hypothalamic RNA expression in HFHC diet-fed mice to levels statistically indistinguishable from CD mice.

Example 7

HFHC Diet and XPro Modulate Mice Social Behavior

HFHC diet-fed mice displayed sociability deficits demonstrated by decreased exploration of a novel mouse. XPRO1595 reverted this alteration by reducing the percentage of time exploring an empty cup (p=0.0027) and increasing the time spent in social interaction (p=0.0027) in HFHC diet-fed mice (FIGS. 12A-F). No statistical differences were observed in the open field or the marble burying test between experimental groups.

INDUSTRIAL APPLICABILITY

The invention is applicable to the medical industry as providing compositions and methods for treatment of complications related to acute or chronic hyperglycemia, more particularly, insulin resistance.

---

We claim:

1. A method for treating complications related to acute or chronic hyperglycemia, the method comprising, in a patient presenting with one or more of said complications selected from diabetes mellitus, insulin resistance, hepatic steatosis, non-alcoholic hepatic steatosis, fibrotic liver disease, vascular disease, or intestinal inflammation:
   determining a level of lipocalin-2 (LCN2) in a patient; and
   if the level of LCN2 is greater than a predetermined-value, then
   administering to the patient a therapeutically effective amount of a selective inhibitor of soluble tumor necrosis factor alpha (solTNF-α), the selective inhibitor of solTNF-a being selected as one which inhibits solTNF-α without inhibiting transmembrane TNF-α, wherein the selective inhibitor of solTNF-a comprises: a dominant negative tumor necrosis factor (DN-TNF)-α protein, a nucleic acid encoding the DN-TNF-α protein, or a combination thereof,
   whereby said complications are treated.

2. The method of claim 1, wherein the level of LCN2 comprises one of: a urine-derived LCN2 level; a serum-derived LCN2 level; a plasma-derived LCN2 level; or a saliva-derived LCN2 level.

3. The method of claim 2, wherein the level of LCN2 comprises a urine-derived LCN2 level and the predetermined value comprises 20 ng/mL.

4. The method of claim 2, wherein the level of LCN2 comprises a serum-derived LCN2 level and the predetermined value comprises 140 ng/mL.

5. The method of claim 2, wherein the level of LCN2 comprises a plasma-derived LCN2 level and the predetermined value comprises 110 ng/mL.

6. The method of claim 2, wherein the level of LCN2 comprises a saliva-derived LCN2 level and the predetermined value comprises 500 ng/mL.

7. The method of claim 1, wherein the DN-TNF-α protein comprises XPRO1595.

8. The method of claim 7, wherein the method comprises administering XPRO1595 in a dose between 0.1 mg/kg and 10.0 mg/kg.

9. The method of claim 1, wherein the DN-TNF-α protein is administered: intravenously; subcutaneously; orally; via aerosol; via topical application; or via gene therapy.

10. The method of claim 1, wherein the DN-TNF-α protein is administered via gene modified autologous or allogeneic cellular therapy.

11. The method of claim 10, wherein the gene therapy comprises mesenchymal stem cells expressing a construct of the DN-TNF-α protein.

12. The method of claim 2, 3, 4, 5, 6, 7, 8, 9, 10, or 11, further comprising:
   measuring one or more markers of inflammation, wherein each of said one or more markers of inflammation is selected from the group consisting of: C-reactive protein (CRP), interleukin 6 (IL-6); tumor necrosis alpha (TNF-alpha); lipocalin 2 (LCN-2); myeloid-derived suppressor cells (MDSCs); Eotaxin, Eotaxin-3, Flt -1/VEGFR-1, ICAM-1, IFN-γ, IL-1α, IL-1β, IL-10, IL-12/IL-23p40, IL-13, IL-15, IL-16, IL-17A, IL-2, IL-4, IL-5, IL-7, IL-8, IP-10, MCP-1, MCP-4, MCP-5, MDC, MIP-1α, MIP-1β, PlGF, SAA, TARC, Tie-2, VCAM-1, VEGF-A, VEGF-C, VEGF-D, FGF, fractalkine, 6Ckine/Exodus-2/SLC/MIP-3, GCP-2, TECK, IP-10, CINC 2, and prostaglandins; and
   administering the DN-TNF-α protein only if the one or more markers of inflammation confirm inflammation in the patient.

13. A method of treating hepatic steatosis in a patient having elevated lipocalin-2 (LCN2), the method comprising:
   determining a level of LCN2 in the patient; and
   if the level of LCN2 is greater than a predetermined-value, then
   administering to the patient a therapeutically effective amount of a selective inhibitor of soluble tumor necrosis factor alpha (solTNF-α), the selective inhibitor of solTNF-α being selected as one which inhibits solTNF-α without inhibiting transmembrane TNF-α, wherein the selective inhibitor of solTNF-α comprises a dominant negative tumor necrosis factor (DN-TNF)-α protein, a nucleic acid encoding the DN-TNF-α protein, or a combination thereof, wherein the DN-TNF-α protein comprises the amino acid sequence of native TNF-α as shown in SEQ ID NO: 3 modified with at least one amino acid substitution selected from the group of substitutions consisting of: V1M, Q21C, Q21R, E23C, N30D, R31C, R31I, R31D, R31E, R32D, R32E, R32S, A33E, N34E, N34V, A35S, D45C, L57F, L57W, L57Y, K65D, K65E, K65I, K65M, K65N, K65Q), K65T, K65S, K65V, K65W, G66K, G66Q, Q67D, Q67K, Q67R, Q67S, Q67W, Q67Y, C69V, L75E, L75K, L75Q), A84V, S86Q, S86R, Y87H, YSTR, V91E, 197R, 197T, C101A, A111R, A111E, K112D, K112E, Y115D, Y115E, Y115F, Y115H, Y115I, Y115K, Y115L, Y115M, Y115N, Y115Q, Y115R, Y115S, Y115T, Y115W, D140K, D140R, D143E, D143K, D143L, D143R, D143N, D143Q, D143R, D143S, F144N, A145D, A145E, A145F, A145H, A145K, A145M, A145N, A145Q, A145R, A145S, A145T, A145Y, E146K, E146L, E146M, E146N, E146R, E146S and S147R
   whereby said patient is treated.

14. The method of claim 13, wherein
the level of LCN2 comprises a urine-derived LCN2 level and the predetermined value comprises 20 ng/ml,
the level of LCN2 comprises a serum-derived LCN2 level and the predetermined value comprises 140 ng/ml;
the level of LCN2 comprises a plasma-derived LCN2 level and the predetermined value comprises 110 ng/ml; or
the level of LCN2 comprises a saliva-derived LCN2 level and the predetermined value comprises 500 ng/ml.

15. The method of claim 13, wherein the DN-TNF-α protein comprises XPRO1595.

16. The method of claim 15, wherein the method comprises administering XPRO1595 in a dose between 0.1 mg/kg and 10.0 mg/kg.

17. The method of claim 16, wherein the DN-TNF-α protein is administered: intravenously, subcutaneously, orally, via aerosol, via topical application, or via gene therapy.

* * * * *